(12) United States Patent
Sendelius et al.

(10) Patent No.: US 11,766,639 B2
(45) Date of Patent: Sep. 26, 2023

(54) WATER PURIFICATION APPARATUS AND METHODS FOR CLEANING THE WATER PURIFICATION APPARATUS

(71) Applicants: Baxter International Inc., Deerfield, IL (US); Baxter Healthcare SA, Glattpark (CH)

(72) Inventors: Peter Sendelius, Staffanstorp (SE); Henrik Lindgren, Genarp (SE); Olof Jansson, Vellinge (SE); Carl-Henry Örndal, Eslöv (SE); Per-Ola Wictor, Stehag (SE); Robert Hallström, Lund (SE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 694 days.

(21) Appl. No.: 16/618,996

(22) PCT Filed: May 15, 2018

(86) PCT No.: PCT/EP2018/062462
§ 371 (c)(1),
(2) Date: Dec. 3, 2019

(87) PCT Pub. No.: WO2018/228765
PCT Pub. Date: Dec. 20, 2018

(65) Prior Publication Data
US 2020/0129927 A1   Apr. 30, 2020

(30) Foreign Application Priority Data
Jun. 15, 2017 (SE) .................................... 1750759-1

(51) Int. Cl.
*B01D 65/02* (2006.01)
*A61M 1/16* (2006.01)
(Continued)

(52) U.S. Cl.
CPC ......... *B01D 65/027* (2013.01); *A61M 1/1686* (2013.01); *A61M 1/1688* (2014.02);
(Continued)

(58) Field of Classification Search
CPC .... B01D 65/027; B01D 61/025; B01D 61/08; B01D 61/12; B01D 61/48; B01D 65/022;
(Continued)

(56) References Cited

U.S. PATENT DOCUMENTS

| 5,032,265 A | 7/1991 | Jha et al. |
| 10,398,823 B2 * | 9/2019 | Heinemann ......... A61M 1/1682 |

(Continued)

FOREIGN PATENT DOCUMENTS

| DE | 102009057562 A1 | 6/2011 |
| WO | WO 2017042319 A1 | 3/2017 |

OTHER PUBLICATIONS

International Search Report; International Application No. PCT/EP2018/062462; dated Nov. 23, 2018; 6 Pages.

(Continued)

*Primary Examiner* — Terry K Cecil
(74) *Attorney, Agent, or Firm* — K&L Gates LLP

(57) ABSTRACT

A water purification apparatus (300) capable of being cleaned at a point of care, and methods for cleaning the water purification apparatus (300) at the point of care. The water purification apparatus (300) and the methods provide an efficient use of a heater (302) for heat disinfection the water purification apparatus (300), e.g. by recirculating heated fluid to further heat the fluid. Several different cleaning programs are provided that may be utilized for cleaning different parts of the water purification apparatus (300).

30 Claims, 11 Drawing Sheets

(51) Int. Cl.
*B01D 61/02* (2006.01)
*B01D 61/08* (2006.01)
*B01D 61/12* (2006.01)
*B01D 61/48* (2006.01)
*C02F 1/00* (2023.01)
*C02F 1/44* (2023.01)
*C02F 1/469* (2023.01)
*C02F 1/28* (2023.01)
*C02F 101/12* (2006.01)
*C02F 101/36* (2006.01)
*C02F 103/02* (2006.01)

(52) U.S. Cl.
CPC ........... *B01D 61/025* (2013.01); *B01D 61/08* (2013.01); *B01D 61/12* (2013.01); *B01D 61/48* (2013.01); *B01D 65/022* (2013.01); *C02F 1/008* (2013.01); *C02F 1/441* (2013.01); *C02F 1/4695* (2013.01); *B01D 2311/25* (2013.01); *B01D 2311/2626* (2013.01); *B01D 2311/2649* (2013.01); *B01D 2311/2684* (2013.01); *B01D 2321/08* (2013.01); *C02F 1/001* (2013.01); *C02F 1/283* (2013.01); *C02F 2101/12* (2013.01); *C02F 2101/36* (2013.01); *C02F 2103/026* (2013.01); *C02F 2209/02* (2013.01); *C02F 2209/40* (2013.01); *C02F 2209/44* (2013.01); *C02F 2301/046* (2013.01); *C02F 2303/04* (2013.01)

(58) Field of Classification Search
CPC ........ B01D 2311/25; B01D 2311/2626; B01D 2311/2649; B01D 2311/2684; B01D 2321/08; B01D 61/422; B01D 61/58; A61M 1/1686; A61M 1/1688; A61M 1/1664; A61M 1/1672; A61M 1/166; A61M 2205/12; A61M 2205/3368; A61M 2205/3653; A61M 2205/7518; A61M 1/1656; A61M 1/28; C02F 1/008; C02F 1/441; C02F 1/4695; C02F 1/001; C02F 1/283; C02F 2101/12; C02F 2101/36; C02F 2103/026; C02F 2209/02; C02F 2209/40; C02F 2209/44; C02F 2301/046; C02F 2303/04; C02F 2303/20; C02F 9/005; C02F 1/42; C02F 5/08; C02F 2101/306; C02F 2201/006; C02F 2209/008; C02F 2303/22; C02F 1/02
See application file for complete search history.

(56) References Cited

U.S. PATENT DOCUMENTS

| | | |
|---|---|---|
| 2007/0102357 A1 | 5/2007 | Weatherill |
| 2015/0231571 A1 | 8/2015 | Volker |
| 2015/0273090 A1 | 10/2015 | Felding et al. |
| 2016/0159672 A1 | 6/2016 | Yokoi et al. |
| 2017/0021308 A1 | 1/2017 | Volker |

OTHER PUBLICATIONS

Written Opinion of the International Searching Authority; International Application No. PCT/EP2018/062462; dated Nov. 23, 2018; 12 Pages.

* cited by examiner

WATER PURIFICATION APPARATUS AND METHODS FOR CLEANING THE WATER PURIFICATION APPARATUS

PRIORITY CLAIM

The present application is a National Phase of International Application No. PCT/EP2018/062462, filed May 15, 2018, which claims priority to SE Application No. 1750759-1, filed Jun. 15, 2017, the entire contents of each of which are incorporated herein by reference and relied upon.

TECHNICAL FIELD

The present disclosure relates to a water purification apparatus and to corresponding methods for cleaning the water purification apparatus including heat disinfection and in some embodiments a cleaning agent. The present invention also relates to a computer program and a computer program product implementing the methods.

BACKGROUND

In treatment of patients suffering acute or chronic renal insufficiency, dialysis therapy is employed. Three general categories of dialysis therapy are hemodialysis, HD, peritoneal dialysis, PD, and continuous renal replacement therapy, CRRT.

In hemodialysis, the patient's blood is cleansed by passage through an artificial kidney in an extracorporeal membrane system, incorporated in a dialysis machine. The blood treatment involves extracorporeal circulation through an exchanger having a semipermeable membrane (dialyzer) in which the patient's blood is circulated on one side of the membrane and a dialysis fluid, comprising the main electrolytes of the blood in concentrations close to those in the blood of a healthy subject, is circulated on the other side. Furthermore, a pressure difference is created between the two compartments of the dialyzer which are delimited by the semipermeable membrane, so that a fraction of the plasma fluid passes by ultrafiltration through the membrane into the compartment containing the dialysis fluid.

CRRT is used as an alternative therapy for patients who are too ill or unstable for standard hemodialysis. It is similar to hemodialysis and makes use of a semipermeable membrane for diffusion and to some extent convection. It is however a slower form of blood treatment than hemodialysis, and may be continuously ongoing from a couple of hours up to several days.

In peritoneal dialysis, dialysis fluid is infused into the patient's peritoneal cavity. This cavity is lined by the peritoneal membrane which is highly vascularized. The metabolites are removed from the patient's blood by diffusion across the peritoneal membrane into the dialysis fluid. Excess fluid, i.e. water is also removed by osmosis induced by a hypertonic dialysis fluid. Through these two processes, diffusion and osmotic ultrafiltration, appropriate quantities of solute metabolites and fluid need to be removed to maintain the patient's body fluid volumes and composition within appropriate limits.

There are various types of peritoneal dialysis therapies, including continuous ambulatory peritoneal dialysis ("CAPD"), automated peritoneal dialysis ("APD"), including tidal flow APD, and continuous flow peritoneal dialysis ("CFPD").

CAPD is a manual dialysis treatment. The patient connects manually an implanted catheter to a drain, allowing spent dialysate fluid to drain from the peritoneal cavity. The patient then connects the catheter to a bag of fresh dialysis fluid, infusing fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from the dialysis fluid source, through the catheter, into the patient's peritoneal cavity and allow the dialysis fluid to dwell within the cavity and the transfer of waste, toxins and excess water to take place. APD machines pump spent dialysate from the peritoneal cavity, through the catheter, to the drain. As with the manual process, several drain, fill and dwell cycles occur during APD. A "last fill" occurs often at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all the fluid from the patient over a longer period of time, a portion of the fluid is removed and replaced after smaller increments of time.

Continuous flow or CFPD systems clean or regenerate spent dialysate instead of discarding it. CFPD systems are typically more complicated than batch systems.

CAPD, APD (including tidal flow) and CFPD systems can employ a pumping cassette. The pumping cassette typically includes a flexible membrane that is moved mechanically to push and pull dialysis fluid out of and into, respectively, the cassette.

In one form of peritoneal dialysis, an automated cycler is used to infuse and drain dialysis fluid. This form of treatment may be done automatically at night while the patient sleeps. The cycler measures the amount of fluid infused and the amount removed to compute the net fluid removal. The treatment sequence usually begins with an initial drain cycle to empty the peritoneal cavity of spent dialysate. The cycler then performs a series of fill, dwell, and drain cycles, typically finishing with a fill cycle.

Peritoneal dialysis generally requires large volumes of dialysis fluid. Generally, at each application, or exchange, a given patient will infuse 2 to 3 liters of dialysis fluid into the peritoneal cavity. The dialysis fluid is allowed to dwell for approximately 1 to 3 hours, at which time it is drained out and exchanged for fresh dialysis fluid. Generally, four such exchanges are performed daily. Therefore, approximately 8 to 20 liters of dialysis fluid is required per day, 7 days a week, 365 days a year for each patient.

Dialysis fluids, for use in the above-mentioned treatments, have traditionally been provided in sealed container bag, ready for use. For example, peritoneal dialysis is typically performed using bags with three different concentration of dextrose. The bags are being delivered to a patient's home as 1 liter to 6 liter bags with different dextrose concentrations. A normal daily consumption is around 8 to 20 liters of PD dialysis fluid. The fluid is provided in sterilized bags of sizes up to six liters, which are packed into boxes and delivered, e.g., monthly, for use to the patient's home. The boxes of fluid may be cumbersome and heavy for PD patients to handle, and consume a substantial space in a room of their homes. The bags and boxes also produce a relatively large amount of waste disposed of on a weekly or monthly basis.

In light of above, several problems become apparent. Shipping and storage of the sheer volume of fluids required is space consuming. Additionally, the use of multiple pre-filled bags produces waste materials in the form of empty containers and packaging.

Sub-systems for an overall peritoneal dialysis, PD, system that creates dialysis solution at the point of use, e.g., at the PD machine are therefore needed.

PD dialysis fluid is delivered directly to the patient's peritoneal cavity. PD fluid therefore needs to have a level of sterilization suitable for being introduced into the patient's peritoneum. PD dialysis fluid is accordingly premixed and sterilized typically prior to delivery to the location of use, usually the patient's home.

Also, in hemodialysis and CRRT, systems that create dialysis solution at the point of use, e.g., at the hemodialysis machine or CRRT machine, are therefore needed.

An overall system for hemodialysis, PD or CRRT, in some embodiments, include three primary components, namely a dialysis machine, a water purifier and a disposable set operating with both the dialysis machine and the water purifier. The dialysis machine is e.g. a PD cycler, a hemodialysis machine or a CRRT machine. The dialysis machine prepares dialysis fluid from purified water from the water purifier and concentrates.

The water purifier produces purified water from e.g. tap water, at the point of use of the purified water.

It is of great importance that the microbial status of the water purifier is excellent. In order to achieve this, the water purifier has to be cleaned and disinfected on a timely basis. Heat disinfection is a suitable method for disinfecting fluid paths of a water purifier that produces water to be used in dialysis. However, for heat disinfection power is needed and at a point of care, for example at a patient's home, power supply may be limited.

SUMMARY

In is an object of the disclosure to provide a water purification apparatus capable to clean itself to a microbial acceptable level at the point of care. It is a further object of the disclosure to provide methods for cleaning the water purification apparatus at the point of care. In detail, it is an object of the disclosure to provide a water purification apparatus and methods for cleaning the same that makes use of heat disinfection and an efficient use of the heating resource in the water purification apparatus for providing the heat disinfection.

These objects and others are at least partly achieved by the apparatuses and methods according to the independent claims, and by the embodiments of the dependent claims.

According to a first aspect, the disclosure relates to a water purification apparatus for producing purified water. The water purification apparatus comprises a Reverse Osmosis, RO, device, arranged to produce a purified fluid flow and a reject fluid flow. RO-device comprises a feed inlet, a permeate outlet and a reject outlet. The water purification apparatus also comprises a feed fluid path arranged with a RO-pump to pump feed fluid to the feed inlet, a heater arranged to heat the purified fluid produced by the RO-device downstream the RO-device, a first fluid path arranged to circulate heated purified fluid from a point downstream the heater to a tank arranged in the feed fluid path inside the water purification apparatus, a second fluid path arranged to transport the heated purified fluid inside the water purification apparatus, a valve arrangement arranged to direct the heated purified fluid into the first fluid path or the second fluid path and a control unit configured to control cleaning of the water purification apparatus. The control unit is configured to cause the water purification apparatus to control heating, with the heater, of the purified fluid from the RO-device and to control the valve arrangement to re-circulate the heated purified fluid in the first fluid path, until a first temperature dependent criterion is fulfilled. The control unit is further configured to cause the water purification apparatus to control the valve arrangement to re-direct the heated purified fluid to flow in a second fluid path of the water purification apparatus, in response to the first temperature dependent criterion is fulfilled, and to control heating, with the heater, of the re-directed heated purified fluid in order to fulfil a second temperature dependent disinfection criterion for the second fluid path.

The water purification apparatus according to the first aspect provides efficient heating of the purified fluid from the RO-device, by recirculating the heated purified fluid to upstream the RO-device such that the heated purified fluid is again heated by the heater. Thereby only one heater downstream the RO-device is needed to heat disinfect the whole fluid path of the water purification apparatus that need to be heat disinfected. Further, a low power consuming heater may be used for heating, whereby the household power at a point of care is not overutilized. The water purification apparatus may comprise at least two paths that each recirculate water to the feed fluid path. By first heating and recirculating the water in only one of them, e.g. the one having the longest flow path, the whole apparatus and thus the other flow paths will also be warmed. The recirculated water is collected in a tank and thus mixed with cooler water, before being again fed to the RO-membrane. The RO-membrane may thus not be exposed to temperatures above 40° C. during the recirculation in the first fluid path, even though the permeate water is heated to a greater temperature downstream the RO-membrane. In one embodiment, no fresh fluid is allowed to enter the water purification apparatus during the recirculation of heated purified fluid. Thereby the re-circulated purified fluid is not mixed with fresh, colder water, but only mixed with the water already in the tank, and the heating of the purified fluid may be performed more rapidly. By redirecting the heated fluid to a second fluid path, more parts of the fluid circuit may become heat disinfected in an energy efficient way. The second fluid path may include the RO-membrane, and the RO membrane may thus be heat disinfected. In some embodiments, by interrupting the recirculation when the first temperature dependent criterion is fulfilled, and directing the heated fluid to a second fluid path that does not include the RO-membrane, it can be avoided to expose the RO-membrane of the RO-device for excessive heating, which may degrade the RO-membrane, and still make use of the same heater to continue heating the purified fluid such that other parts of the fluid path of the water purification apparatus may be heat disinfected without affecting the RO-membrane. Further, by heating the RO-membrane, it becomes more permeable and will let more particles through, which might affect the performance of downstream located components. By controlling the heating and directing the heated purified fluid appropriately, both the RO-membrane and downstream located components may be spared.

The inventors have discovered that some parts of the water purification apparatus need to be cleaned less frequent than other parts. In more detail, a permeate side of the water purification apparatus needs to be cleaned more frequently, than a feed side of the water purification apparatus and the fluid paths that lead fluid back to the feed side. The feed side and the permeate side are partitioned by the RO-membrane of the RO-device. A fully functional RO-membrane does not let bacteria through. Therefore, it is considered possible to disinfect the feed side and the fluid paths that leads permeate fluid back to the feed side less frequently than the permeate side. The proposed water purification apparatus is capable of directing the heated fluid to different fluid paths, whereby different fluid paths may be cleaned with different frequency. The inventors have also realized that by carrying out the cleaning in different flow paths that are cleaned separately and after each other, it can also be assured that the heated water reaches all parts of each flow path as an appropriate pressure and/or flow rate in each flow path can be assured, and thus controlled.

In some embodiments, a cleaning agent is distributed in the fluid path of the water purification apparatus during the heat disinfection. The cleaning agent is then distributed in the heated fluid and may enhance the cleaning effect of the heated fluid.

According to some embodiments, the first temperature dependent criterion comprises to re-circulate the heated purified fluid in the first fluid path, until a first temperature dependent disinfection criterion is fulfilled. Thus, according to some embodiments, the first temperature dependent criterion is a first temperature dependent disinfection criterion. Thus, the first fluid path might include components such as valves, lines, an RO-membrane etc. that should be heat disinfected. The purified fluid is then e.g. heated to a predetermined temperature for a predetermined time, such that a disinfection criterion is fulfilled for each component of the first fluid path that should be heat disinfected. In one embodiment, the temperature for disinfecting the RO-membrane is achieved in a last step of the recirculation. Alternatively, the RO-membrane is only warmed up to 40° Celsius, but the purified fluid is heated to 70°-95° Celsius. This because the purified fluid will be mixed with water of lower temperatures in the tank before being pumped to the RO-membrane. The feed water will thus have a temperature of up to 40° Celsius.

According to some embodiments, the apparatus comprises a first temperature sensor arranged to measure a temperature of the purified fluid in the first fluid path, and wherein the first temperature dependent criterion comprises to control heating, based on the measured temperature, of the purified fluid such that a temperature of the purified fluid is within a range of 70-95° Celsius. The first temperature sensor is arranged to sense the temperature of the heated purified fluid downstream the heater. For example, the first temperature sensor may be arranged to sense the temperature of the heated purified fluid directly after the heater. Then the temperature of the heated purified fluid may be easily monitored, and the effect to the heater regulated such that the RO-membrane is not overheated or the heated fluid starts boiling. In other embodiments, the first temperature sensor is arranged to measure the temperature of the heated purified fluid, seen from the heater, in downstream locations, in order to monitor such that a disinfection criterion is fulfilled.

According to some embodiments, the apparatus comprises a first flow sensor arranged to measure a flow rate of the purified fluid; and wherein the first temperature dependent criterion comprises to control heating of the purified fluid, and pumping with the RO-pump, based on the measured temperature and the measured flow rate, such that the purified fluid obtains a predetermined temperature dependent flow rate. Thereby also the flow rate of the purified fluid may be regulated to achieve a certain temperature of the purified fluid. As described, when the RO-membrane becomes warmer, it also becomes more permeable and more fluid, and also particles, are let through. By increasing the flow rate of the RO-pump, more fluid may be forced through the RO-membrane such that more purified fluid may be heated faster. For example, if the purified fluid has been heated to a high temperature, e.g. 85° C., the power to the heater has to be lowered to not overheat the purified fluid when crossing the heater. However, if the flow rate of the purified fluid is increased, more fluid can be heated without overheating, and the power to the heater may be reduced less resulting in a faster heating of the total amount of the fluid that is recirculated.

According to some embodiments, the water purification apparatus comprises a second temperature sensor arranged to measure the temperature of the purified fluid in the second fluid path, and wherein the control unit is configured to determine, based on the measured temperature, a time duration for heat disinfecting the second fluid path with the fluid at the measured temperature, such that a bacterial reduction criterion is fulfilled, and to control heat disinfection of the second fluid path based on the time duration such that the bacterial reduction criterion is fulfilled. Thus, by measuring the temperature in the second fluid path, the fulfillment of the disinfection criterion of second fluid path may be accurately monitored and controlled. The temperature is in one embodiment continuously monitored.

According to some embodiments, the water purification apparatus comprises a port in fluid communication with the second fluid path, the port being arranged to be connected to a fluid line set, and wherein the second temperature dependent disinfection criterion is, or comprises to fulfil, a temperature dependent disinfection criterion for the port. Thereby, the fulfillment of the disinfection criterion of the port may be accurately monitored and controlled.

According to some embodiments, the second fluid path comprises a drain path, and wherein the second temperature dependent disinfection criterion is, or comprises to fulfil, a temperature dependent disinfection criterion for the drain path. Thereby, the fulfillment of the disinfection criterion of the drain path may be accurately monitored and controlled.

According to some embodiments, the first fluid path or the second fluid path comprises a polishing-device. According to one embodiment, the polisher-device comprises an electrodeionization unit, EDI-device, comprising a product channel and a concentrate channel. According to an alternative embodiment, the polisher-device comprises a mixed bed. The control unit is configured to cause the water purification apparatus to perform a polisher-device disinfection, e.g. an EDI-device disinfection. The polisher-device disinfection comprises to control heating of the purified fluid that will flow through the polisher-device, in order to fulfil a temperature dependent disinfection criterion for the polisher-device, and to control the water purification apparatus to bypass the polisher-device, in response to the temperature dependent disinfection criterion for the polisher-device is fulfilled. Thereby, the fulfillment of the disinfection criterion of the polisher-device may be accurately monitored and controlled. After fulfillment of the disinfection criterion of the polisher-device, the polisher-device is thereafter bypassed, to avoid that the performance of the polisher-device is negatively affected.

According to some embodiments, the control unit is configured to cause the water purification apparatus to: control a fluid level in the tank to a predetermined level of the tank, before heating of the purified fluid. The fluid level is for example controlled to a low or medium level, such that the heated fluid has room to expand when heated, without needing to pass fluid to the drain.

According to some embodiments, the control unit is configured to cause the water purification apparatus to perform an active cool down of an RO-membrane of the RO-device. The active cool down comprises to control the RO-pump to pump water from a water source to the RO-device until a predetermined cooling criterion for a reverse osmosis, RO, membrane of the RO-device has been fulfilled, and control the valve arrangement to drain reject fluid from the water purification apparatus. In order to heat disinfect the RO-membrane, the RO-membrane is heated to a temperature between 70-85° C. As the RO-membrane is vulnerable to heat, the RO-membrane is cooled down such that it is exposed to a high temperature for a time period as short as possible.

According to some embodiments, the water purification apparatus comprises a second pump, and wherein the control unit is configured to cause the water purification apparatus to: control the second pump to pump air and control the valve arrangement to direct the air past a closed port of the water purification apparatus in order to remove water from the port. Thereby, none or less fluid will flow from the port when the lid thereafter is opened by the user, e.g. to connect a new fluid line set.

According to some embodiments, the water purification apparatus comprises a second pump arranged for pumping a cleaning agent such as citric acid, wherein the control unit is configured to cause the water purification apparatus to: control the second pump to pump a cleaning agent into the feed fluid path and circulate the cleaning agent in a reject recirculation path from the reject outlet to the feed inlet, in order to remove scaling on an RO-membrane of the RO-device. Thereby, there is less need to pre-treat the feed water with an anti-scaling agent, or other kind of softening methods.

According to some embodiments, the heater is arranged to a permeate fluid line in order to heat the purified fluid produced by the RO-device. Thus, the heater heats the purified fluid flowing from the RO-device. This placement of the heater provides for an efficient use of its heating capability.

According to some embodiments, a disposable line set is in fluid communication with the water purification apparatus, wherein the control unit is configured to cause the water purification apparatus to clean the disposable line set. The cleaning may include one or several of flushing the disposable set with cold water, flushing the disposable line set with a cleaning agent such as citric acid, flushing the disposable line set with heated fluid and/or flushing the disposable line set with heated fluid, where the heated fluid includes the cleaning agent.

According to a second aspect, the disclosure relates to a water purification apparatus comprising a Reverse Osmosis, RO, device, arranged to produce a purified fluid flow and a reject fluid flow. The RO-device comprises a feed inlet, a permeate outlet and a reject outlet. The water purification apparatus also comprises a feed fluid path arranged with a RO-pump to pump feed fluid to the feed inlet, a heater arranged to heat the purified fluid produced by the RO-device downstream the RO-device, a purified fluid path arranged to transport the heated purified fluid, and a polisher-device arranged in the purified fluid path. A second fluid path is arranged to bypass the polisher-device and to transport the heated purified fluid past the polisher-device. A valve arrangement is arranged to direct the heated purified fluid into the purified fluid path or into the second fluid path. The water purification apparatus also comprises a control unit configured to control cleaning of the water purification apparatus and configured to cause the water purification apparatus to: control heating, with the heater, of the purified fluid in the purified fluid path, in order to fulfil a temperature dependent disinfection criterion for the polisher-device; re-directing the purified fluid producing device to bypass the polisher-device, in response to the temperature dependent disinfection criterion for the polisher-device is fulfilled and control heating, with the heater, of the purified fluid in the second fluid path in order to fulfil a temperature dependent disinfection criterion for the second fluid path.

The described water purification apparatus provides a way of properly heat disinfecting the polisher-device, without exposing it for excessive heating that might degrade the capacity of the same. In one embodiment, the polisher-device comprises an EDI-device. In another embodiment, the polisher-device comprises a mixed bed.

According to some embodiments, the second fluid path comprises a port arranged in fluid communication with the second fluid path, the port being arranged to be connected to a fluid line set, and wherein the second temperature dependent disinfection criterion is, or comprises to fulfil, a temperature dependent disinfection criterion for the port, and/or wherein the second fluid path comprises a drain path and wherein the second temperature dependent disinfection criterion is, or comprises to fulfil, a temperature dependent disinfection criterion for the drain path.

According to some embodiments, the heater is arranged to a permeate fluid line in order to heat the purified fluid produced by the RO-device.

According to some embodiments, the water purification apparatus comprises a heat conserving arrangement arranged to transfer heat from a fluid in a first drain path and/or a fluid in a second drain path, to another medium. fluid in an inlet path, of the water purification apparatus. Thereby energy may be conserved, and the risk of contacting heated fluid is reduced as the drained fluid is cooled down.

According to a third aspect, the disclosure relates to a method for cleaning a water purification apparatus for producing purified water, the water purification apparatus comprises a Reverse Osmosis, RO, device producing a purified fluid flow and a reject fluid flow. The method comprises controlling heating of the purified fluid downstream the RO-device; re-circulating the heated purified fluid in a first fluid path from a point downstream the heater to a tank arranged in a feed fluid path upstream the RO-device, until a first temperature dependent criterion is fulfilled; re-directing the heated purified fluid to flow in a second fluid path of the water purification apparatus, in response to the first temperature dependent criterion being fulfilled; and controlling heating of the re-directed heated purified fluid in order to fulfil a second temperature dependent disinfection criterion for the second fluid path.

The same effects as described with reference to the water purification apparatus may be achieved with the methods.

According to some embodiments, the first temperature dependent criterion comprises re-circulating the heated purified fluid in the first fluid path to the feed fluid path, until a first temperature dependent disinfection criterion is fulfilled.

Thus, according to some embodiments, the first temperature dependent criterion is a first temperature dependent disinfection criterion.

According to some embodiments, the controlling heating and re-circulating comprises: measuring the temperature of the purified fluid in the first fluid path; and wherein the first temperature dependent criterion comprises controlling heating, based on the measured temperature, of the purified fluid such that a temperature of the purified fluid is within a range of 70°-95° Celsius.

According to some embodiments, the controlling heating and re-circulating comprises: measuring a flow rate of the purified fluid; and wherein the first temperature dependent criterion comprises to control heating and pumping with the RO-pump, based on the measured temperature and the measured flow rate, such that the purified fluid obtains a predetermined temperature dependent flow rate.

According to some embodiments, the controlling heating comprises: measuring the temperature of the fluid in the second fluid path; and wherein the method comprises determining, based on the measured temperature, a time duration for heat disinfecting the second fluid path with the fluid at the measured temperature, such that a bacterial reduction criterion is fulfilled, and controlling heat disinfection of the second fluid path based on the time duration such that the bacterial reduction criterion is fulfilled.

According to some embodiments, the water purification apparatus comprises a port in fluid communication with the second fluid path, the port being arranged to be connected to a fluid line set, and wherein the second temperature dependent disinfection criterion is, or comprises to fulfil, a temperature dependent disinfection criterion for the port.

According to some embodiments, the second fluid path comprises a drain path, and wherein the second temperature dependent disinfection criterion is, or comprises to fulfil, a temperature dependent disinfection criterion for the drain path.

According to some embodiments, the first fluid path or the second fluid path comprises a polisher-device, and the method comprises performing an polisher-device comprising: controlling heating of the purified fluid that will flow through the polisher-device, in order to fulfil a temperature dependent disinfection criterion for the polisher-device; controlling the water purification apparatus to bypass the polisher-device, upon the temperature dependent disinfection criterion for the polisher-device is fulfilled.

According to some embodiments, the method comprises controlling a fluid level in a tank arranged in the feed fluid path to a predetermined level of the tank, before heating of the purified fluid.

According to some embodiments, the method comprises performing an active cool down of an RO-membrane of the RO-device, the active cool down comprising: pumping water from a water source to the RO-device until a predetermined cooling criterion for the RO-membrane has been fulfilled; and controlling draining of reject fluid from the water purification apparatus.

According to some embodiments, the method comprises pumping air past a closed port of the purified water producing device in order to remove water from the port.

According to some embodiments, the method comprises circulating a cleaning agent such as citric acid in a reject recirculation path from a reject outlet to a feed inlet of the RO-device, in order to remove scaling on an RO-membrane of the RO-device.

According to some embodiments, the method comprises transferring thermal energy from a fluid in a first drain path and/or a fluid in a second drain path, to another medium. The another medium is for example a fluid in an inlet path of the water purification apparatus, or another fluid in a conserving element, e.g. a closed container with the another fluid.

According to some embodiment, the method comprising cleaning a disposable line set in fluid communication with the water purification apparatus.

According to a fourth aspect, the disclosure relates to a method for cleaning a water purification apparatus for producing purified water, the water purification apparatus comprises a Reverse Osmosis, RO, device producing a purified fluid flow and a reject fluid flow. The method comprises controlling heating of the purified fluid produced by the RO-device downstream the RO-device, directing the heated purified fluid in a first fluid path, through a polisher-device; re-directing the heated purified fluid into a second fluid path to bypass the polisher-device, in response to a temperature dependent disinfection criterion for the polisher-device is fulfilled; controlling heating of the re-directed purified fluid; in order to fulfil a temperature dependent disinfection criterion for the second fluid path.

According to some embodiments, the water purification apparatus comprises a port in fluid communication with the second fluid path, the port being arranged to be connected to a fluid line set, and wherein the second temperature dependent disinfection criterion is, or comprises to fulfil, a temperature dependent disinfection criterion for the port and/or wherein the second fluid path comprises a first drain path, and wherein the second temperature dependent disinfection criterion is, or comprises to fulfil, a temperature dependent disinfection criterion for the drain path.

According to a fifth aspect, the disclosure relates to a computer program comprising instructions which, when the program is executed by a computer, e.g. the control unit of the water purification apparatus, cause the computer to carry out the method according to any one of the embodiments herein.

According to a sixth aspect, the disclosure relates to a computer-readable medium comprising instructions which, when executed by a computer, cause the computer to carry out the method according to any one of the embodiments herein.

DETAILED DESCRIPTION

In the following a water purification apparatus capable for being cleaned at a point of care, where the cleaning includes heat disinfection, and methods for performing the cleaning including heat disinfection, will be explained. In one embodiment, a fluid line set fluidly connected to the water purification apparatus is also cleaned.

The water purification apparatus is capable of producing water for use in dialysis treatment, e.g. for mixing dialysis fluid to be used in the dialysis treatment. In some embodiments, the water purification apparatus is capable of producing water for injection.

The water purification apparatus is in the following explained as a part included in a peritoneal dialysis system. However, the water purification apparatus may be used for producing purified water to other kinds of dialysis systems, e.g. hemodialysis or CRRT systems, for use in production of dialysis fluids to be used in the hemodialysis or CRRT treatments performed by the systems at a point of care or point of use.

Figure 1:
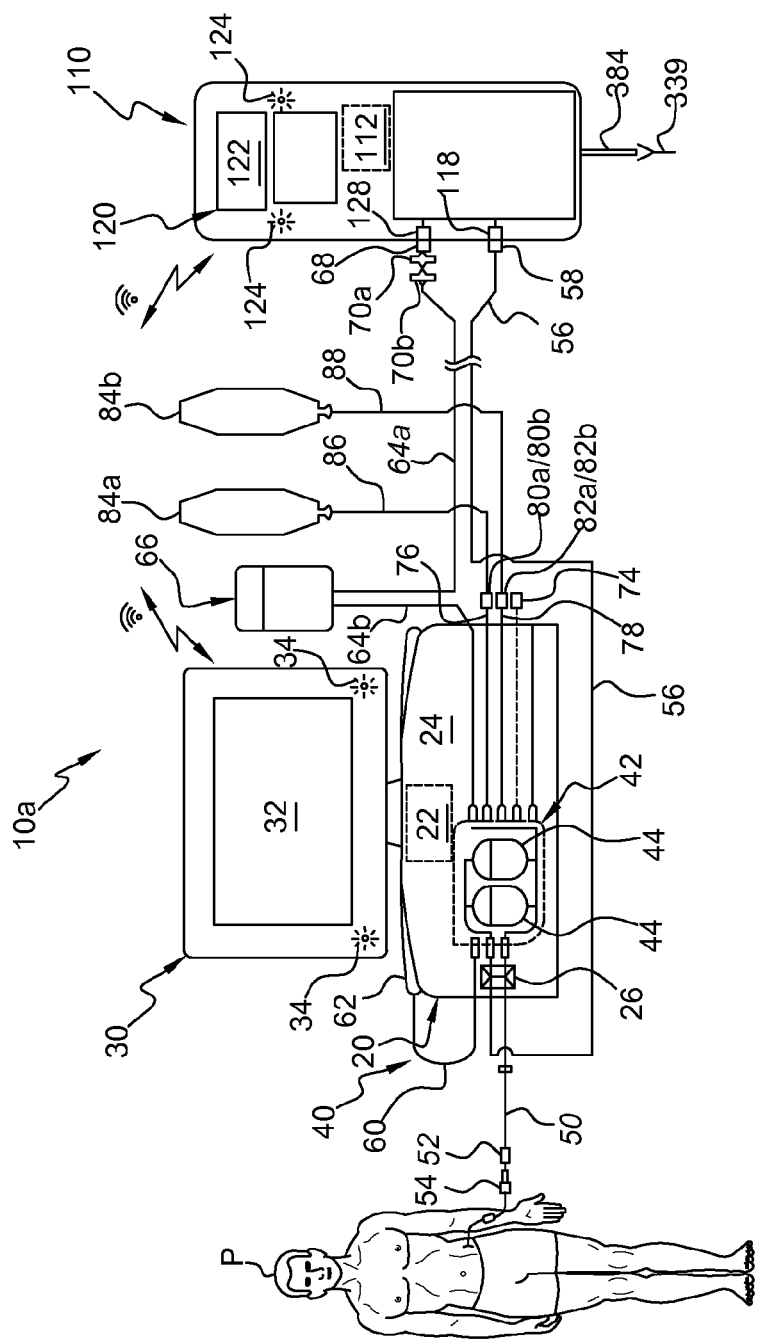
FIG. 1 is a front elevation view of one embodiment of a PD dialysis system having point of care dialysis fluid production using purified water from a water purification apparatus.

Referring now to the drawings and in particular to FIG. 1, one embodiment of a peritoneal dialysis system having point of use dialysis fluid production of the present disclosure is illustrated by system 10a. System 10a includes a cycler 20 and a water purification apparatus 300. Suitable cyclers for cycler 20 include, e.g., the Amia® or HomeChoice® cycler marketed by Baxter International Inc., with the understanding that those cyclers need updated programming to perform and use the point of use dialysis fluid produced according to system 10a. To this end, cycler 20 includes a control unit 22 having at least one processor and at least one memory. Control unit 22 further includes a wired or wireless transceiver for sending information to and receiving information from a water purification apparatus 300. Water purification apparatus 300 also includes a control unit 112 having at least one processor and at least one memory. Control unit 112 further includes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology. The control unit 22 comprises a computer program comprising instructions which, when the program is executed by the control unit 22, cause the control unit 22 and the water purification apparatus to carry out any one or several of the methods and programs according to any one of the herein disclosed embodiments. The instructions may be saved on a computer-readable medium such as a portable memory device, e.g. a USB memory, a portable computer, or similar, and loaded into the control unit 22.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purification apparatus 300 includes a first drain path 384, leading to a drain 339, which can be a housing drain or drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, for providing positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off solenoid pneumatic valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (viii) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button.

Water purification apparatus 300 in the illustrated embodiment also includes a user interface 120. Control unit 112 of water purification apparatus 300 in an embodiment includes a video controller, which may have its own processing and memory for interacting with primary control processing and memory of control unit 112. User interface 120 includes a video monitor 122, which may likewise operate with a touch screen overlay placed onto video monitor 122 for inputting commands into control unit 112. User interface 120 may also include one or more electromechanical input device, such as a membrane switch or other button. Control unit 112 may further include an audio controller for playing sound files, such as alarm or alert sounds, at one or more speaker 124 of water purification apparatus 300.

Figure 2:
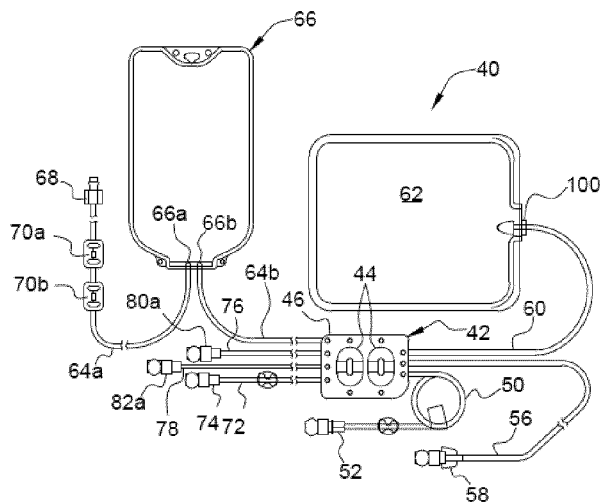
FIG. 2 is an elevation view of one embodiment of a disposable line set used with the system illustrated in FIG. 1.

Referring additionally to FIG. 2, one embodiment of disposable line set 40 is illustrated. Disposable line set 40 is also illustrated in FIG. 1, mated to cycler 20 to move fluid within the disposable line set 40, e.g., to mix dialysis fluid as discussed herein. Disposable line set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable line set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable line set 40 includes a drain line 56 that extends from a drain line port of cassette 42 and terminates at a drain line connector 58. FIG. 1 illustrates that drain line connector 58 connects removably to a drain port 118 of water purification apparatus 300.

FIGS. 1 and 2 further illustrate that disposable set 40 includes a heater/mixing line 60 that extends from a heater/mixing line port of cassette 42 and terminates at a heater/mixing bag 62 discussed in more detail below. Disposable set 40 includes an upstream water line segment 64a that extends to a water inlet 66a (FIG. 2) of water accumulator 66. A downstream water line segment 64b extends from a water outlet 66b (FIG. 2) of water accumulator 66 to cassette 42. In the illustrated embodiment, upstream water line segment 64a begins at a water line connector 68 and is located upstream from water accumulator 66. FIG. 1 illustrates that water line connector 68 is removably connected to a water outlet, i.e. the product port 128 of water purifier 110.

Water purification apparatus 300 outputs purified water and water suitable for e.g. peritoneal dialysis ("WFPD"). WFPD is water suitable for making dialysis fluid for delivery to the peritoneal cavity of patient P. WFPD is for example water for dialysis or water for injection.

In one embodiment, a sterile sterilizing grade filter 70a is placed upstream from a downstream sterile sterilizing grade filter 70b. Filters 70a and 70b may be placed in water line segment 64a upstream of water accumulator 66. Sterile sterilizing grade filters 70a and 70b may be pass-through filters that do not have a reject line. Pore sizes for sterilizing filter may, for example, be less than a micron, such as 0.1 or 0.2 micron. Suitable sterile sterilizing grade filters 70a and 70b may, for example, be Pall IV-5 or GVS Speedflow filters, or be filters provided by the assignee of the present disclosure. In alternative embodiments, only one or more than two sterile sterilizing grade filter are placed in water line segment 64a upstream of water accumulator 66. The one or several sterile sterilizing grade filters may be arranged close to the water accumulator 66, such that the fluid line set 40 becomes easier to fold. In further alternative embodiments, there are no sterile sterilizing grade filters in the water line segment 64a. The sterile sterilizing grade filters may for example be replaced by one or several ultrafilters located in the product fluid path of the water purification apparatus 300.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first concentrate line 76 extending from a first concentrate port of cassette 42 and terminates at a first cassette concentrate connector 80a. A second concentrate line 78 extends from a second concentrate port of cassette 42 and terminates at a second cassette concentrate connector 82a.

FIG. 1 illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

In an embodiment, to begin treatment, patient P loads cassette 42 into cycler and in a random or designated order (i) places heater/mixing bag 62 onto cycler 20, (ii) connects upstream water line segment 64a to product port 128 of water purification apparatus 300, (iii) connects drain line 56 to drain port 118 of water purification apparatus 300, (iv) connects first cassette concentrate connector 80a to first container concentrate connector 80b, and (v) connects second cassette concentrate connector 82a to second container concentrate connector 82b. At this point, patient connector 52 is still capped. Once fresh dialysis fluid is prepared and verified, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

The water purification apparatus 300 is in the following described in more detail.

Schematic of Functional Parts of Water Purification Apparatus

Figure 3:
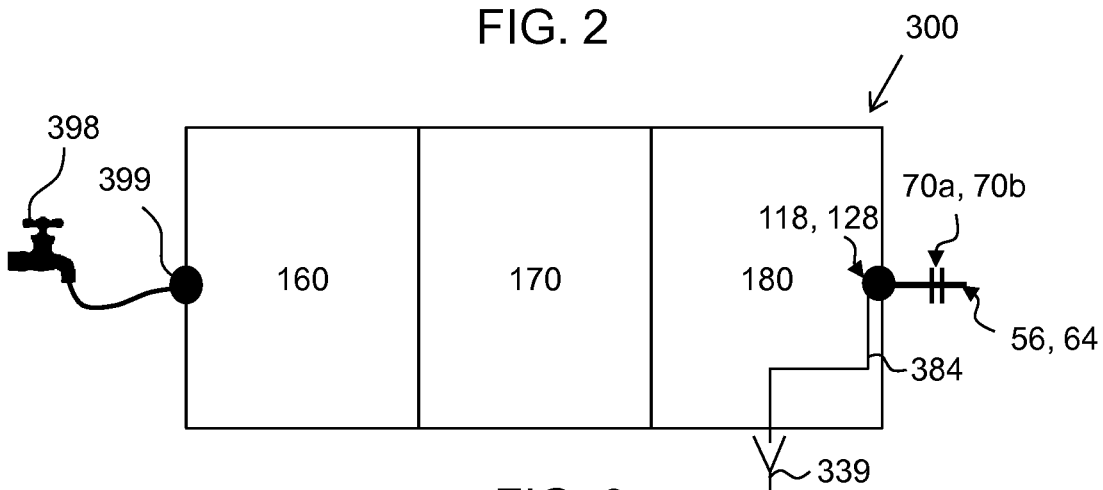
FIG. 3 is a schematic of some functional parts of the water purification apparatus.

In FIG. 3 is a schematic of the functional parts of the water purification apparatus 300 according to one embodiment, including a pre-treatment module 160, a reverse-osmosis (RO) module 170 and a post-treatment module 180. The water purification apparatus 300 comprises an inlet port 399 for feeding water from a water source 398, e.g. a water tap, into the water purification apparatus 300, for purification of the water. The incoming water from the water source is fed through the inlet port 399 into the pre-treatment module 160.

The Pre-Treatment Module

The Pre-treatment module 160 treats the incoming water with a particle filter and a bed of activated carbon.

The particle filter is arranged to remove particles such as clay, silt and silicon from the incoming water. The particle filter is arranged to prohibit particles in the size of micro meter, optionally also larger endotoxin molecules, from the incoming water.

The bed of activated carbon is arranged to remove chlorine and compositions with chlorine from the incoming water, and to absorb toxic substances and pesticides. In an example embodiment, the bed of activated carbon is arranged to remove one or several of hypochlorite, chloramine and chlorine. In a further example embodiment, the bed of activated carbon is also arranged to reduce organic compounds (TOC total organic carbon) including pesticides of the incoming water.

In some embodiments, the particle filter and the bed of activated carbon are integrated in one single consumable part. The consumable part is for example exchanged on a predefined interval dependent on the incoming water quality. The quality of the incoming water is for example examined and determined by qualified people before the first use of the water purification apparatus 300 at a point of care.

Optionally the pre-treatment module 160 comprises an ion exchange device for protection of downstream located devices such as a Reverse Osmosis, RO, membrane and a polisher.

The pre-treatment module 160 thus filters the incoming water and delivers pre-treated water to a downstream located RO-module 170.

RO-Module

The RO-module 170 removes impurities from the filtered water, such as microorganisms, pyrogens and ionic material from the pre-treated water by the effect of reverse osmosis. The pre-treated water is pressurized by a pump and forced through RO-membrane to overcome the osmotic pressure. The RO-membrane is for example a semi-permeable membrane. Thereby the stream of pre-treated water, called feed water, is divided into a reject stream of water and a stream of permeate water. In an example embodiment, the reject water may be passed via a one or both of a first reject path and a second reject path. The first reject path recirculates reject water back to the feed fluid path of the RO-pump in order to be fed back into RO-device again. The recirculated reject water increases the feed flow to the RO-device, to get a sufficient flow past the reject side of the RO-membrane to minimize scaling and fouling of the RO-membrane. The second reject path directs reject water to drain. This makes the concentration level on the reject side to be sufficiently low to get an appropriate, required, permeate fluid concentration. If the feed water has low content of solutes, part of the drain flow can also be directed back to the inlet side of the RO-membrane and thereby increasing the water efficiency of the water purification apparatus 300.

The RO-module 170 thus treats the pre-treated water and delivers permeate water to a downstream located post-treatment module 180.

Post-Treatment Module

The post-treatment module 180 polishes the permeate water in order to further remove ions from the permeate water. The permeate water is polished using a polisher device such as an Electrodeionization, EDI, device or a mixed bed filter device.

The EDI-device makes use of electrodeionization for removing ions, from the permeate water, such as aluminum, lead, cadmium, chromium, sodium and/or potassium etc., which have penetrated the RO-membrane. The EDI-device utilizes electricity, ion exchange membranes and resin to deionize the permeate water and separate dissolved ions, i.e. impurities, from the permeate water. The EDI-device produce polished water, polished by the EDI-device to a higher purity level than the purity level of the permeate water. The EDI has an anti-bacterial effect of the product water and can reduce the amount of bacteria and endotoxins in the water due to, among other, the electrical field in the EDI-device.

The mixed bed filter device comprises a column, or container, with a mixed bed ion exchange material.

The polished water, herein also referred to as product water, is thereafter ready for being delivered from a product port 128 of the water purification apparatus 300 to a point of use of the product water. The product water is suitable for dialysis, i.e. water for dialysis. In one embodiment, the product water is water for injection. In an example embodiment, a disposable line set 40, including a drain line 56, is arranged to the water purification apparatus 300 for transporting the product water to a point of use. Optionally, the water purification apparatus 300 comprises a drain port 118. The drain port 118 is in one example embodiment used for receiving used fluid, e.g. from a PD patient, via a drain line 64, for further transport via a first drain path 384 inside the water purification apparatus 300 to a drain 339 of the water purification apparatus 300. As a further option, the drain port 118 receives a sample of ready mixed solution for further transport to a conductivity sensor arranged in the water purification apparatus 300, e.g. in the first drain path 384. The disposable line set 40 is here arranged with a sterilized sterile filter set 70*a*, 70*b*, for filtering the product water from the water purification apparatus 300 to ensure a quality of the product water as of water for injection.

Thus, the product water collected in the accumulator bag 66 has passed through one or several sterile sterilizing grade filters of the disposable line set 40 for removal of bacteria and endotoxins, i.e. to produce sterile product water. According to one embodiment, the sterile sterilizing grade filters are redundant.

By collecting the sterile product water in the accumulator bag 66, the water purification apparatus 300 and the cycler 20 are decoupled in terms of pressure, so that the high pressure needed to push water through the sterile sterilizing grade filters does not affect the cycler 20.

EDI

Figure 4:
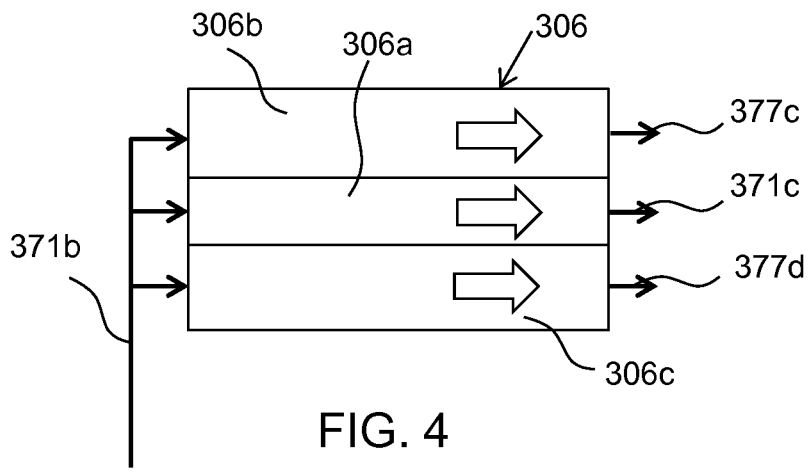
FIG. 4 is a schematic of an electrodeionization device according to one embodiment.

In FIG. 4 a schematic of an example embodiment an EDI-device 306 is illustrated. The EDI-device 306 comprises one or more product channels 306*a*, two or more concentrate channels 306*b*, and one or more electrode channels 306*c*. However, the EDI-device 306 is for simplicity referred to as having one product channel 306*a*, one concentrate channel 306*b* and one electrode channel 306*c*. Permeate water is fed to all the channels via a polisher fluid path 371*b*. The produced product water is outputted from the product channel 306*a* into a product fluid path 371*c*. The concentrate water from the concentrate channel 306*b*, which contains ions removed from the permeate water to produce product water, is outputted to a concentrate fluid path 377*c*. The electrode fluid from the electrode channel 306*c*, which contains gas etc., is outputted to an electrode fluid path 377*d*. The concentrate water and electrode fluid is for example passed to drain 339 or recirculated to the tank 350 for reuse. The concentrate fluid path 377*c* and the electrode fluid path 377*d* may debouch into the same fluid path, herein referred to as the concentrate fluid path 377*c*.

Introduction to Cleaning

The control unit 112 of the water purification apparatus 300 is arranged to set the water purification apparatus 300 in different operating states. The water purification apparatus 300 is arranged to act upon commands from the cycler 20.

The water purification apparatus 300 is, when not in use but powered on, set in a standby state.

When a treatment is finished, for example a PD-treatment, the dialysis machine or cycler 20 sends a message to the water purification apparatus 300 in order for the water purification apparatus 300 to set itself ready for disconnection of the disposable line set 40 and to make sure a port lid 401 (the port lid 401 covering and the product port 128 and drain port 118 from the outside, and at the same time connects the product port 128 and the drain port 118) is closed. The water purification apparatus 300 then checks that the port lid 401 for the ports 118, 128 is closed. For example, may a sensing circuit comprising a contact sensor 345 (see FIG. 13), such as a Hall-sensor, be present in a wall of the water purification apparatus 300, to sense the closing of the port lid 401, and send a closed lid signal to the control unit 112 if the port lid 401 is closed.

It is of great importance that the microbial status of RO module 170 and the post-treatment module 180 of the water purification apparatus 300 is excellent. In order to achieve this, the water purification apparatus 300 runs cleaning programs on a timely basis. The heat disinfection programs included in the cleaning are in some embodiments based on the following principle. Heating aims at preventing growth of bacteria on the internal surfaces of the fluid path of the water purification apparatus 300. In order to achieve a sufficient reduction of organisms, the heat disinfection is in some embodiments based on the "A0 concept". The A0 concept will be explained in more detail in the following. The A0 concept defines the dose of heat disinfection. "Fluid path or flow path of the water purification apparatus 300" according to one embodiment includes all the different flow paths or fluid paths making up the RO module 170 and the post-treatment module 180 of the water purification apparatus 300. Thus, in this embodiment, the pre-treatment fluid path connecting the inlet port 333 with the water tank 350, and a tank air vent line 325 (overflow connection) to drain 339, if any (See FIG. 13), are not heat disinfected.

The cleaning programs can either be scheduled for automatic start or manually started from a user interface menu or service interface of the water purification apparatus 300. After an interrupted cleaning program, the water purification apparatus 300 will go back to the state standby, where it will be noted that there still need to be performed a cleaning and restart the program.

Some parts of the water purification apparatus 300 are part of the RO-membrane feed side and of fluid paths that leads permeate fluid back to the feed side. The RO-membrane feed side includes the tank 350, the feed fluid path 391, the RO-pump 450, the parts of the RO-device upstream the RO-membrane 324 and reject fluid paths 389, 385b and the components therein. These parts need to be cleaned frequently. However, between these parts and the permeate side stands the RO-membrane. The permeate side includes the fluid paths that lead to the ports 118, 128 and the first drain path 384 and the components therein, i.e. the fluid paths that do not lead permeate fluid back to the feed side. A fully functional RO-membrane does not let bacteria through. Therefore, it is considered possible to disinfect these parts of the water purification apparatus 300 (thus the RO-membrane feed side and of fluid paths that leads permeate fluid back to the feed side) less frequently than the permeate side. The disinfection frequency need however be such that the bacterial growth is kept acceptable low. E.g. no biofilm is tolerated in the fluid path of the RO module 170 and the post-treatment module 180 of the water purification apparatus 300. But, as long as this can be achieved, all parts except the parts leading directly to the product port 128, are considered to require less frequent disinfection than the product port 128 itself and the parts leading directly to the product port 128.

The first drain path 384 of the water purification apparatus 300 may be in contact with patient fluid, possibly containing e.g. proteins, fibrin material and other substances that may grow onto the walls of the fluid path, for example when used dialysis fluid is passed via the first drain path 384 to drain 339. Hence, even if this part only receives fluid, bacteria can grow and possibly climb up the first drain path 384 to the cassette 42 of the disposable line set 40. It is therefore important that this part of the water purification apparatus 300 is also cleaned frequently. According to some embodiments, the ports 118, 128 and the first drain path 384 are cleaned and/or disinfected after every treatment to prevent growth.

Figure 5:
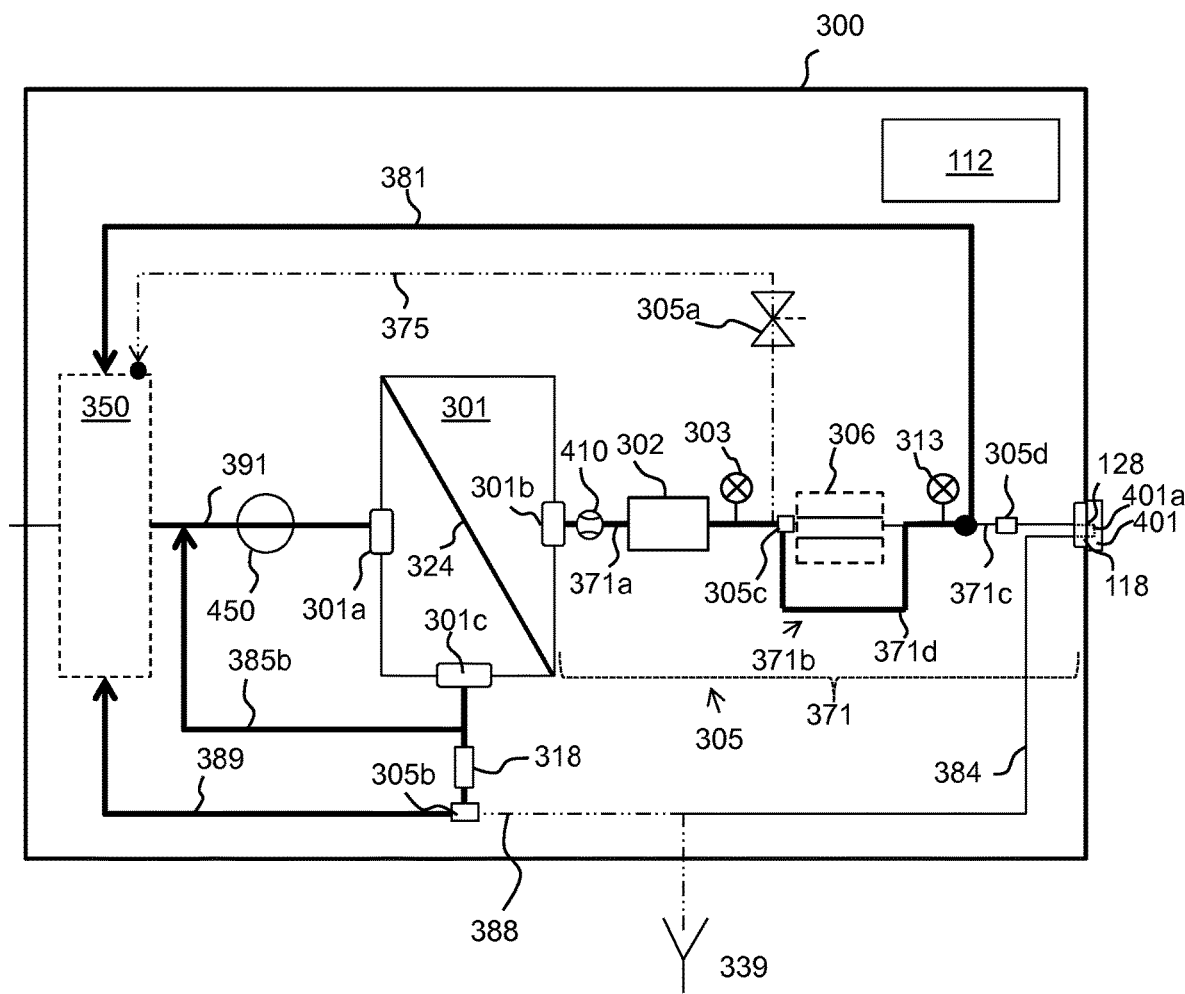
FIG. 5 is a schematic illustration of a of a water purification apparatus according to a first exemplary embodiment.
Figure 6:
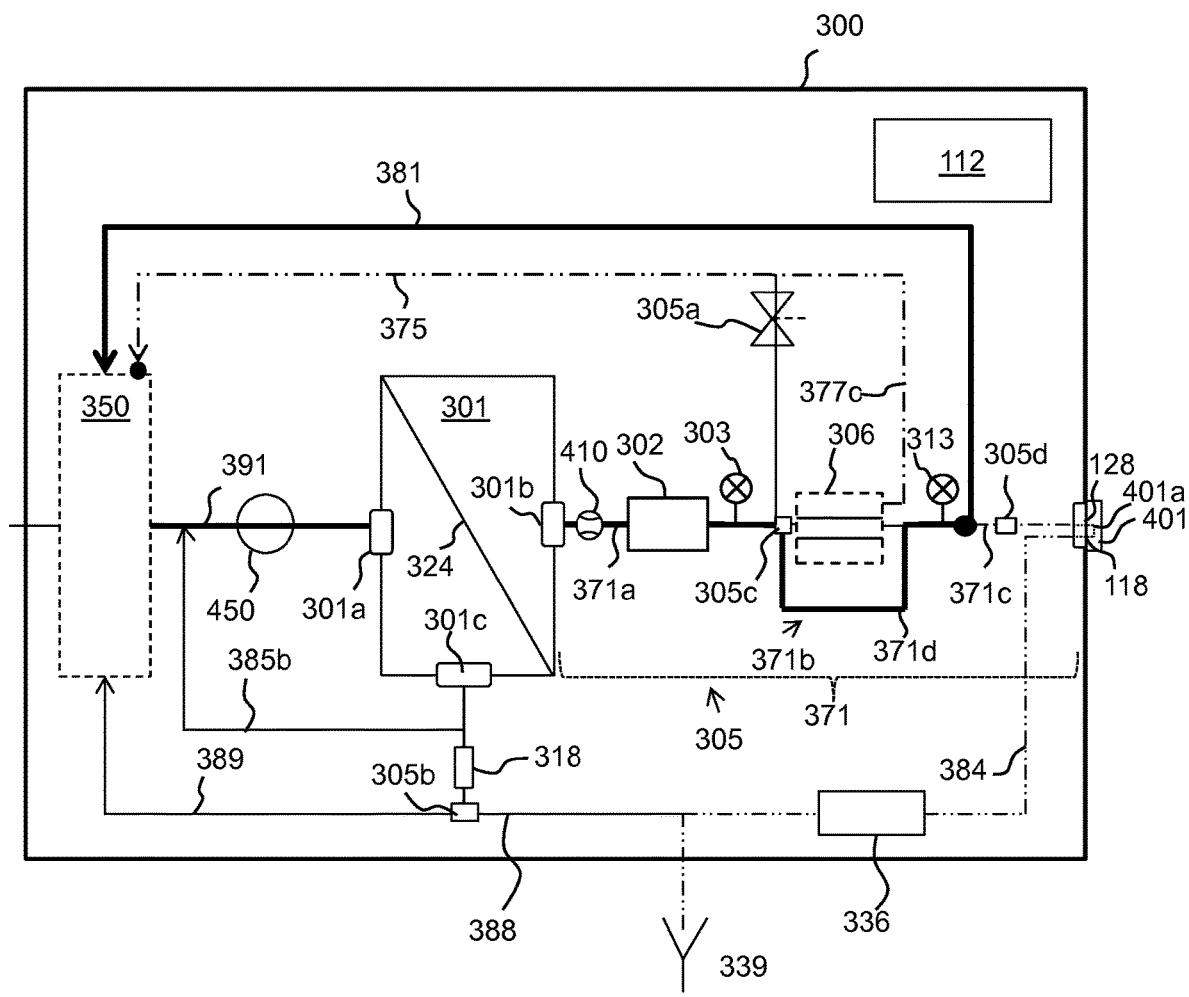
FIG. 6 is a schematic illustration of a of a water purification apparatus according to a second exemplary embodiment.
Figure 7:
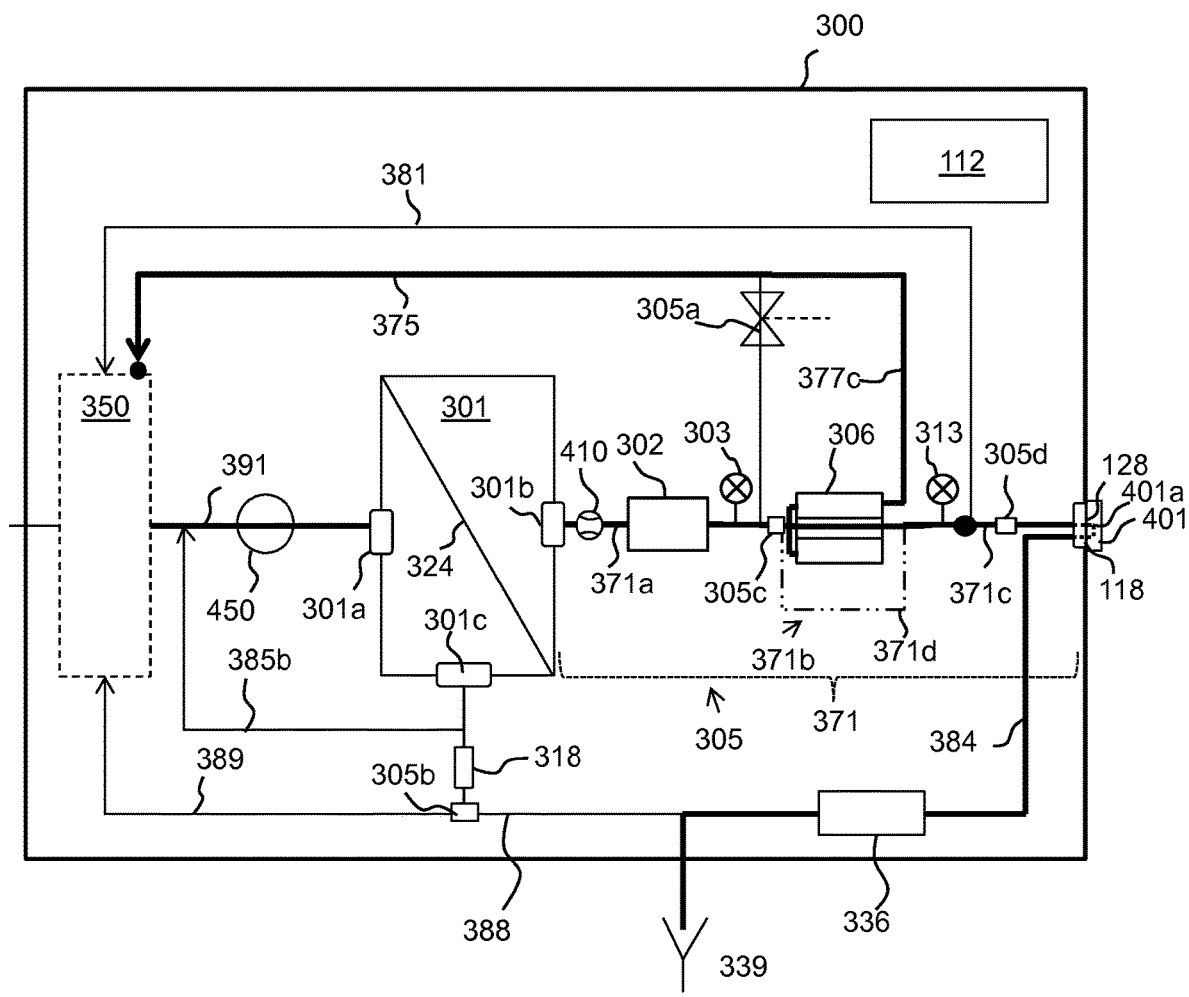
FIG. 7 is a schematic illustration of a of a water purification apparatus according to a third exemplary embodiment.
Figure 8:
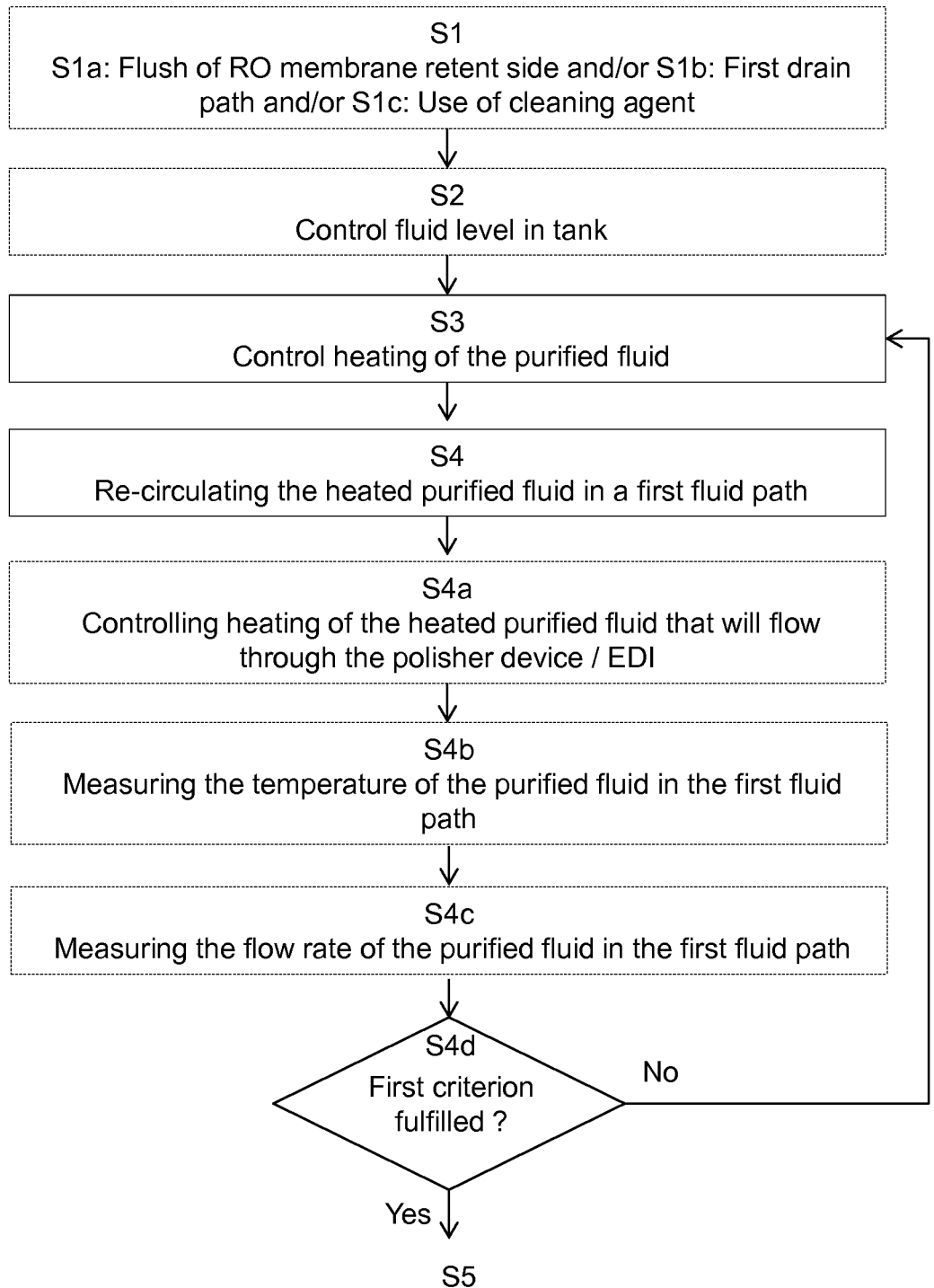
FIGS. 8-12 illustrate steps of the cleaning method according to some embodiments.
Figure 9:
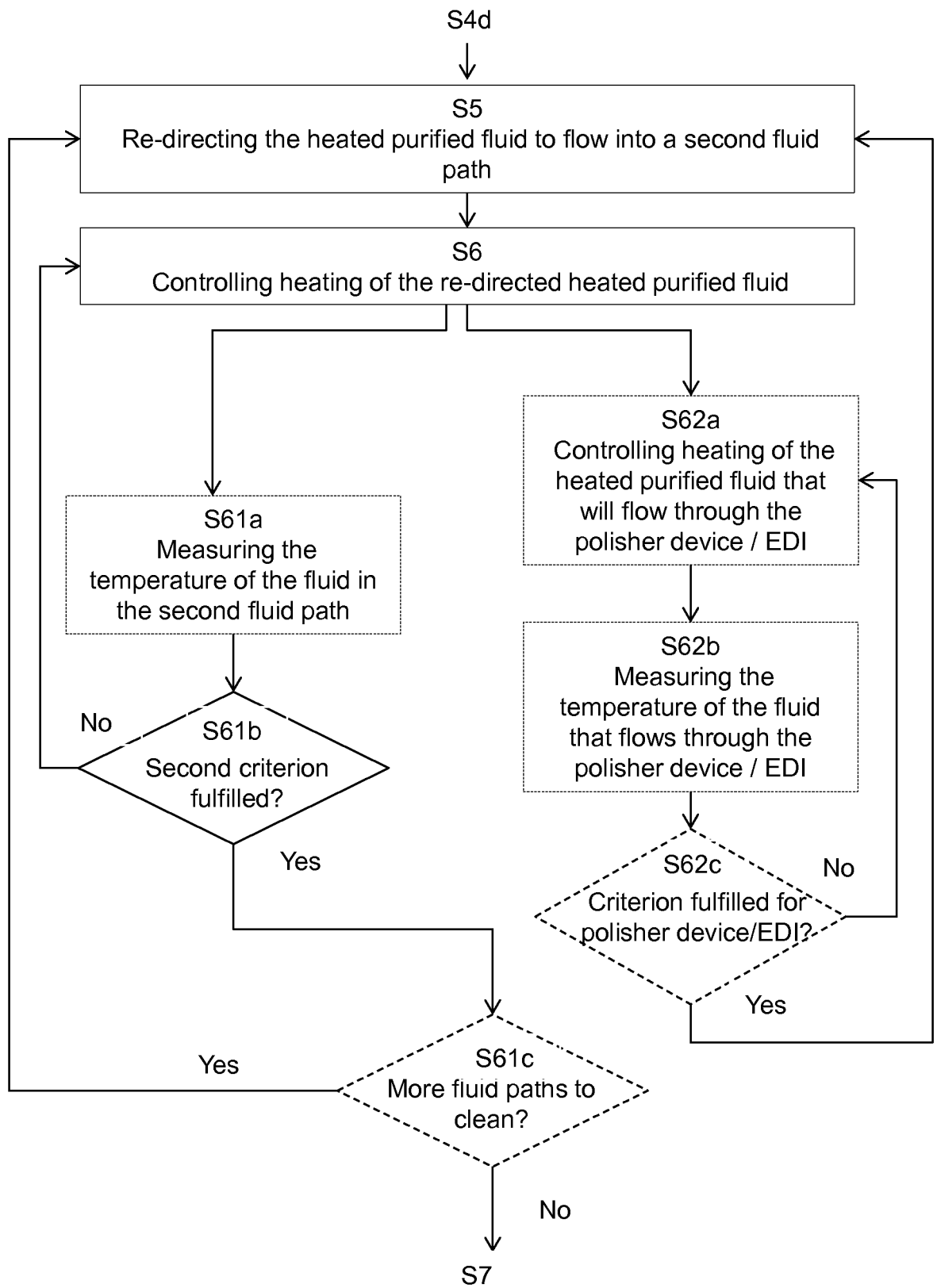
Figure 10:
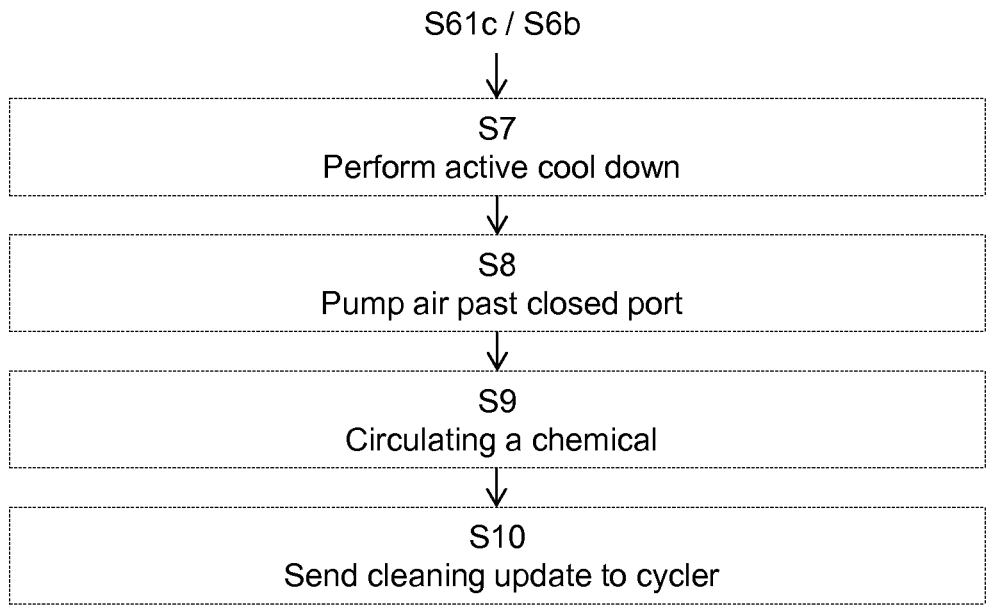

According to some embodiments, the water purification apparatus 300 is programmed to know and to schedule when and how to run the different disinfection programs. In order to, as far as possible, protect the components of the water purification apparatus 300, for increased reliability, and to prevent bacterial growth, a number of different cleaning and disinfection programs are provided by the water purification apparatus 300. Some of these embodiments will be explained in the following. Note that FIGS. 5-7 are conceptual drawings that only illustrates parts of the water purification apparatus 300 that are related to the proposed technique. A more detailed illustration of an exemplary water purification apparatus 300 is provided in relation to FIG. 13.

During cleaning of the water purification apparatus 300, a cleaning agent such as citric acid is in some embodiments introduced into the flow of water, and therefore it is here referred to "fluid" instead of purely water. The purified fluid flow is thus in some embodiments a purified water flow, and the reject fluid flow a reject water flow.

FIG. 5 illustrates a first exemplary embodiment of a water purification apparatus 300. Further below, a method for cleaning the fluid path of the water purification apparatus 300 in FIG. 5 during a general disinfection will be explained, with reference to the flowchart of FIGS. 8-12.

The differences in line style of the fluid paths of FIG. 5 illustrate the main flows in a first fluid path (thicker lines) and a second fluid path (dash double dot line), during a general disinfection.

With reference now to FIG. 5, the RO-device 301 is arranged to produce a purified fluid flow and a reject fluid flow. In greater detail, the RO-device 301 comprises a feed inlet 301a, a permeate outlet 301b and a reject outlet 301c. The RO-membrane 324 separates the feed inlet 301a and the reject outlet 301c, from the permeate outlet 301b. A feed fluid path 391 is connected to the feed inlet 301a, in order to transport feed fluid to the feed inlet 301a. The feed fluid path 391 is arranged with a tank 350 for collecting fluid, and a RO-pump 450, arranged to pump feed fluid to the feed inlet 301a. The RO-pump 450 is arranged downstream the tank 350. The RO-pump 450 is configured to be controlled to a certain pump rate corresponding to a certain flow rate of the permeate fluid. As the permeability of the RO-membrane 324 increases as the temperature of the feed fluid increases, the relationship between the pump rate and the flow rate is dependent on the temperature of the feed fluid, and thus the temperature of the RO-membrane 324. In one alternative embodiment, the tank 350 is not present.

The water purification apparatus 300 further comprises a purified fluid path 371, connected to the permeate outlet 301b and to the product port 128, in order to transport purified fluid from the permeate outlet 301b to the product port 128. The purified fluid path 371 comprises the permeate fluid path 371a, a polisher fluid path 371b and a product fluid path 371c. The polisher fluid path 371b comprises a polisher-device 306, for example an EDI-device or a mixed bed filter device. A bypass path 371d is arranged to bypass the polisher device. A three-way valve 305c is arranged to be controlled by the control unit 112 to direct the permeate fluid flow selectively to either into the polisher-device 306, or into the bypass path 371d in order to bypass the polisher-device 306. A first drain path 384 is connected to the drain port 118 and to the drain 339, in order to pass fluid from the drain port 118 to the drain 339. The first drain path 384 here embodies the part of a cycler drain path that is present inside the water purification apparatus 300. The first drain path is arranged for example to transport drained PD-solution from the patient to the drain 339 of the water purification apparatus 300.

The water purification apparatus 300 is further arranged with a heater 302 arranged to heat the purified fluid produced by the RO-device 301 downstream the RO-device 301. The heater 302 may for example include a heating element. A first recirculation path 381, is arranged to circulate heated purified fluid from a point downstream the RO-device 301 and downstream the heater 302, to the feed fluid path 391, inside the water purification apparatus 300. The first recirculation path 381 is in some embodiments referred to as a first fluid path. The heated purified fluid is here recirculated to the tank 350 and again fed to the feed inlet 301a of the RO-device 301. However, the heated purified fluid is alternatively recirculated directly to the fluid line upstream the RO-pump 450.

Initially, before the heating included in the cleaning program is started, the fluid level in the tank 350 may be controlled to a predetermined level of the tank 350. This may be achieved by monitoring the fluid level in the tank, and controlling the inlet valve 332 and/or the tank valve 328 (see FIG. 13).

The reject flow is feed back to the feed fluid path 391 via a first reject path 385b. The first reject path 385b is connected with, and in fluid communication with, the reject outlet 301c and the feed fluid path 391. A second reject path 389, is connected with, and in fluid communication with, the reject outlet 301c and here the tank 350. However, the second reject path 389 is alternatively connected with and in fluid communication with the feed fluid path 391. A second drain path 388 is arranged to feed reject fluid from the reject outlet 301c to a drain 339. A three-way valve 305b is arranged to selectively direct the reject flow into either the second reject path 389 or into the second drain path 388. A constant flow device 318 is arranged to control the flow rate in the second reject path upstream the three-way valve 305b. The described reject flow arrangement controls the balance between the permeate flow, the reject flow and the pump rate of the RO-pump 450, dependent on the permeability of the RO-membrane 324.

The water purification apparatus 3000 comprises a second recirculation path 375 arranged with a flow control device 305a. In one example embodiment, the second recirculation path 375 is referred to as a second fluid path. The second recirculation path 375 is arranged to transport the heated purified fluid inside the water purification apparatus 300. In an exemplary embodiment, the second drain path 388 is also referred to as a second fluid path.

The control unit 112 is configured to control cleaning and in particular disinfection of the water purification apparatus 300. This means to control cleaning of all, or parts of, the parts of the fluid path of the RO module 170 and post-treatment module 180 of the water purification apparatus 300 that are in contact with fluid. A fluid path is here meant to include tubes, lines, channels, inside of apparatuses, ports, the tank, components such as valves, control devices etc. of the water purification apparatus 300.

The control unit 112 is configured to cause the water purification apparatus 300 to control heating, with the heater 302, of the purified fluid from the RO-device 301. The heater 302 comprises for example a heating rod. In one example embodiment, part of the permeate fluid path 371a is wound around the heating rod, in order to heat the purified fluid in the permeate fluid path 371a efficiently. Alternatively, the heater 302 comprises a heat exchanger, arranged to exchange heat between a heating medium and the fluid in permeate fluid path 371a. The heater 302 is in one embodiment configured to heat the purified fluid with a certain heating rate. By controlling the power to the heater 302, and thus the power of the heater, the heating rate of the heater 302 can be regulated. The heating rate is however also dependent on the flow rate of the purified fluid.

A valve arrangement 305 is arranged to direct the heated purified fluid into the first fluid path or the second fluid path. The valve arrangement 305 comprises for example, but not limited to, one or several of: the flow control device 305a, the three-way valve 305b, a three-way valve 305c and a product water valve 305d.

The water purification apparatus 300 may comprise one or several temperature sensors, e.g. a first and a second temperature sensor.

In FIG. 5 a permeate temperature sensor 303 is arranged to measure a temperature of the purified fluid, thus the permeate fluid, in the permeate fluid path 371a downstream the heater 302. When the heated permeate fluid is directed to the first recirculation path 381, the temperature of the heated permeate indicates the temperature of the fluid in the first recirculation path 381.

Furthermore, a product fluid temperature sensor 313 is arranged to measure the temperature of the product fluid, thus the temperature of the fluid in the product fluid path 371c.

A flow sensor 410 is arranged to measure a flow rate of the purified fluid. The flow sensor 410 is here arranged to the permeate fluid path 371a and is arranged to measure the flow rate of the permeate fluid from the RO-device 301. The flow sensor 410 is arranged downstream the permeate outlet 301b, and upstream the heater 302, for example directly downstream the RO-device 301.

For cleaning the water purification apparatus 300, the control unit 112 is configured to control the valve arrangement 305 to re-circulate the heated purified fluid in a first fluid path, e.g. the first recirculation path 381, until a first temperature dependent criterion is fulfilled. The first temperature dependent criterion comprises for example a time duration for the re-circulation, or a predetermined temperature to be achieved during the re-circulation. For example, the first temperature dependent criterion comprises to control heating, based on the temperature measure by the first temperature sensor, of the purified fluid such that the temperature of the purified fluid is within a range of 70°-95° Celsius. According to one embodiment, the first temperature dependent criterion comprises to control heating, based on the temperature measure by the first temperature sensor, of the purified fluid such that the temperature of the purified fluid is within a range of 70°-95° Celsius for a predetermined time period, e.g. 5, 10, 15 or 20 minutes. As the heated purified fluid is recirculated to the tank 350, the heated purified fluid will be mixed with cooler fluid in the tank 350, and the temperature of the fluid in the tank 350 will in one embodiment not go beyond 40° Celsius. The temperature of the RO-membrane 324 will thus not go beyond 40° Celsius as the RO-membrane 324 is warmed by fluid being passed through the RO-membrane fed from the tank 350, which will spare the RO-membrane 324. In one embodiment, the first temperature dependent criterion comprises to control heating of the purified fluid, and pumping with the RO-pump 450, based on the measured temperature and the measured flow rate of the purified fluid, such that the purified fluid obtains a predetermined temperature dependent flow rate. Thus, as the temperature of feed fluid is increased, as it is a mix of heated re-circulated purified fluid and re-circulated reject fluid, the temperature of the RO-membrane 324 also increases. The increased temperature of the RO-membrane 324 makes it more permeable, and more fluid can be forced through the RO-membrane 324. The consequence is decreased purification by the RO-device 301, but as the water purification apparatus 300 is in a cleaning mode, it can be tolerated. In one embodiment, also the RO-membrane is heat disinfected up to a range of 70°-95° Celsius for a predetermined time period, e.g. 5, 10, 15 or 20 minutes. However, according to some other embodiments, the temperature of the RO-membrane 324 should preferably not go beyond a certain temperature, e.g. 40° Celsius. The first recirculation path 381 is in one embodiment the longest and/or outermost recirculation path of the fluid recirculation paths, such that the whole water purification apparatus is heated while recirculating heated water in the first recirculating path 381 which will speed up the subsequent heat disinfection of the remaining fluid paths.

The temperature of the RO-membrane 324 essentially corresponds to the temperature of the permeate fluid before it is heated by the heater 302, and may be estimated by monitoring the power needed by the heater 302 to reach a certain temperature of the heated purified fluid, measured by the permeate temperature sensor 303, see Equation (1) below. In an example embodiment, the power to the heater 302 is set to a certain power level, e.g. a maximum level tolerated by the water purification apparatus 300, and the purified fluid is heated to a predetermined temperature (corresponding to a predetermined RO-membrane temperature) while the heater 302 is powered with the certain power level. When the predetermined temperature of the RO-membrane, alternatively the purified fluid, has been reached, the power to the heater 302 is reduced, in order to not overheat the RO-membrane and/or cause the fluid start boiling. The predetermined temperature of the RO-membrane is in one embodiment 40 Celsius. In an alternative embodiment, the predetermined temperature of the RO-membrane is 70°-85° Celsius. However, as the power is reduced, the pump rate of the RO-pump 450 may simultaneously be increased, in order to heat the purified fluid more rapidly to the predetermined temperature. The flow rate of the purified fluid is then monitored, measured by the flow sensor 410, in order to obtain a predetermined flow rate of the purified fluid that is temperature dependent and correlated with the power to the heater 302. The pumping rate of the RO-pump 450 is thus controlled based on the flow rate of the purified fluid, and the power fed to the heater 302.

The temperature of the RO-membrane 324 may be calculated as follows:

$$T_{RO} = T_{permeat} - \frac{P}{Q \cdot cp} \qquad \text{Equation (1)}$$

where P is the power [W] fed to the heater 302, Q is the flow rate [l/s] measured by the flow sensor 410, $T_{permeat}$ is the temperature of the purified fluid measured by the permeate temperature sensor 303, and cp is the specific heat capacity of water, 4.19 kJ/(kg×K). ΔT is the temperature difference from tank 350 to after heater 302: $T_2-T_{RO}$. Thus, by controlling, by the control unit 112, any or both of the power of the heater 302 and the pumping rate of the RO-pump 450, the temperature of the RO-membrane 324, and thus the water in the tank 350, may be controlled to a certain temperature. In addition, the recirculation in the first fluid path may be stopped upon a certain temperature of the RO-membrane 324 being achieved, optionally the recirculation may be maintained for a certain time period in order to heat disinfect the RO-membrane 324.

The recirculation of the fluid aims to use the increase of the temperature of the purified fluid, by returning the heated purified fluid to the feed fluid path 391, and eventually to the tank 350. The energy of the heated fluid is then transferred to the feed fluid and thereby the heating of the purified fluid is faster. The recirculation also has the effect that the whole water purification apparatus 300 will become warm. The heat loss to the environment/surrounding in the coming heat disinfection can then be reduced, and the coming heat disinfection can thus be made faster. According to one embodiment, the inflow to the tank 350 is stopped during the heating, while recirculating the fluid, such that no cold water enters the tank 350. Thereby, the heating may be made faster.

In response to the first temperature dependent criterion being fulfilled, the control unit 112 is configured to control the valve arrangement 305 to re-direct the heated purified fluid to flow into the second fluid path, for example the second recirculation path 375 and/or the second drain path 388, of the water purification apparatus 300. The control unit 112 is further configured to control heating, with the heater 302, of the re-directed heated purified fluid in order to fulfil a second temperature dependent disinfection criterion for the second fluid path. The second temperature dependent disinfection criterion comprises, for example, to achieve a certain temperature of the heated purified fluid in the second fluid path for a certain time period. Alternatively, the second temperature dependent disinfection criterion comprises to simply direct the heated purified fluid to the second fluid path for a certain predetermined time period, that is specific for the second fluid path or for any component to be heat disinfected that is part of, or arranged to, the second fluid path. The second fluid path should thus be exposed to heated purified fluid at a certain temperature for a certain time, in order to heat disinfect the second fluid path.

FIG. 6 illustrates a second exemplary embodiment of a water purification apparatus 300, with fluid paths marked up for illustrating an example of a partial disinfection of the fluid path of the water purification apparatus 300. Further below, a method for cleaning the fluid path of the water purification apparatus 300 of FIG. 6 during the partial disinfection will be explained, with reference to the flowcharts of FIGS. 8-12.

The differences in line style of the fluid paths of FIG. 6 illustrates the main flows in a first fluid path (thicker lines) and a second fluid path (dash double dot line), during the example embodiment of the partial disinfection.

The second exemplary embodiment is essentially the same as the first exemplary embodiment, except that it also comprises a conductivity sensor 336, or conductivity cell, in the first drain path 384. The product port 128 and the drain port 118 are closed by the port lid 401. When the port lid 401 is closed, the product port 128 and the drain port 118 becomes connected by a path 401a, such that heated fluid can flow from the product port 128 and into the drain port 118 and further to the drain 339 via the first drain path 384. According to one embodiment shown in FIGS. 5-7, the path 401a is defined by the port lid 401, and is at least partly included in the port lid 401. According to another embodiment shown in FIG. 13, the path 401a is included in the water purification apparatus 300, and is defined by a separate line connecting the product port 128 and drain port 118. The separate line is not accessible when the port lid 401 is open. When the port lid 401 is closed, the port lid 401 opens up the separate line such that heated fluid may flow from the product port 128 to the drain port 118 via the separate line, in order to disinfect the product port 128 and the drain port 118.

In an example embodiment, the product port 128 and the drain port 118 are in fluid communication with the second fluid path. The second temperature dependent disinfection criterion may then comprise to fulfil a temperature dependent disinfection criterion for the product port 128 and/or the drain port 118, e.g. to fulfill the A0 criterion for the ports 118, 128. In some embodiments, the temperature dependent disinfection criterion comprises a predetermined pressure the heated purified fluid should have in order to properly disinfect the product port 128 and/or the drain port 118, i.e. "the ports 118, 128". The predetermined pressure is for example measured with a pressure sensor (e.g. pressure sensor 308 in FIG. 13) arranged in the product fluid path 371*c*.

In an exemplary embodiment, the second fluid path comprises a drain path, e.g. the first drain path 384, wherein the second temperature dependent disinfection criterion comprises to fulfil a temperature dependent disinfection criterion for the drain path.

In an exemplary embodiment, the temperature should thus be at least 75° C. for a certain predetermined time, in order to fulfil the respective A0 value for the ports 118, 128 and the first drain path 384.

Figure 13:
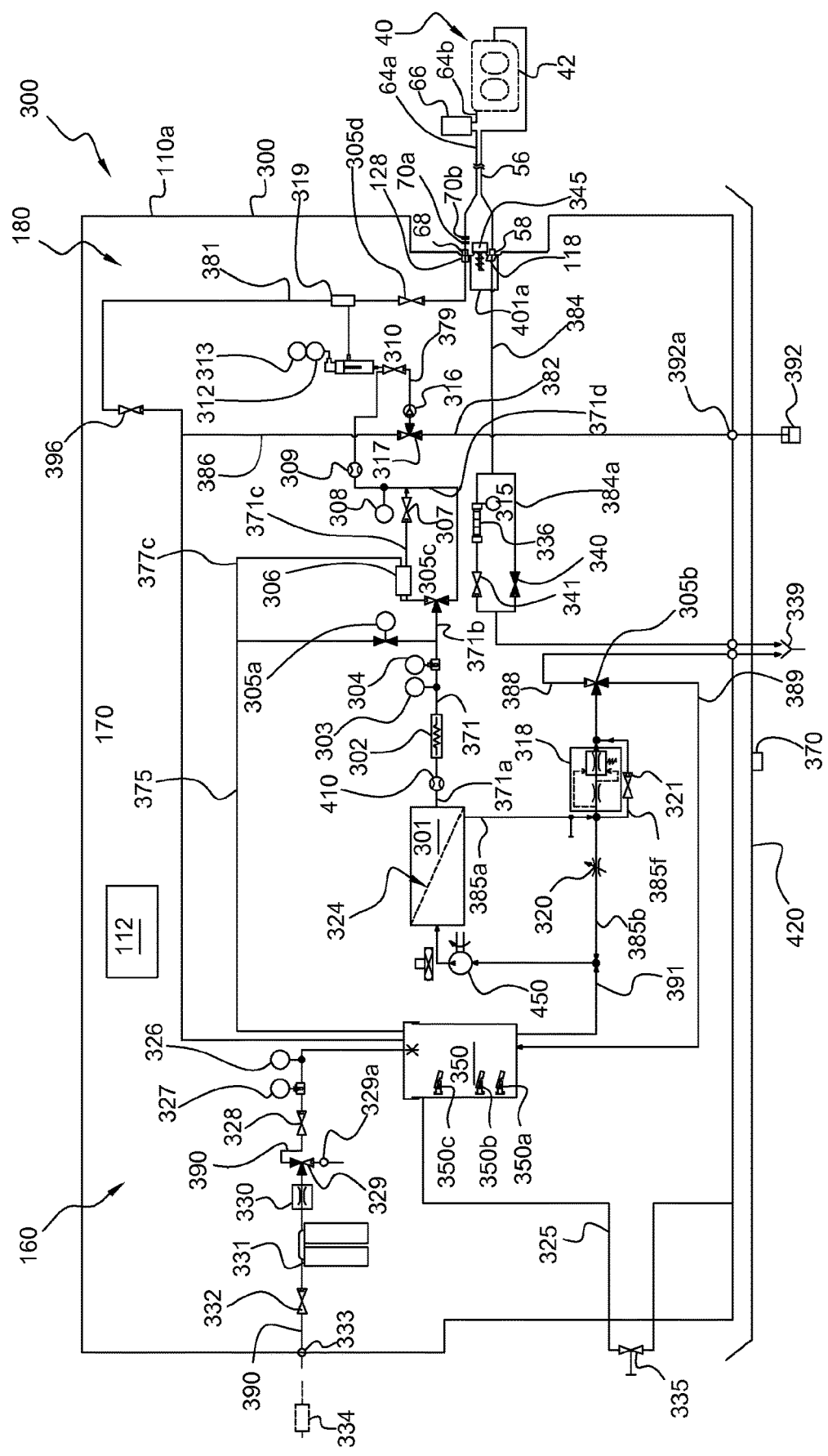
FIG. 13 illustrates an embodiment of the water purification apparatus in greater detail.

In an exemplary embodiment, the control unit 112 is configured to cause the water purification apparatus 300 to perform a polisher-device disinfection, e.g. an EDI-device disinfection. The EDI-device disinfection comprises to control heating of the purified fluid that will flow through the EDI-device 306, and thus through the product channel 306*a* of the EDI-device 306, in order to fulfil a temperature dependent disinfection criterion for the EDI-device 306. The EDI-device disinfection further comprises to control the water purification apparatus 300 to bypass the EDI-device 306, in response to the temperature dependent disinfection criterion for the EDI-device 306 is fulfilled. For example, the control unit 112 is configured to execute an EDI-device disinfection program comprising to control the water purification apparatus 300 to perform the EDI-device disinfection by means of the valve arrangement 305, the heater 302, the first temperature sensor and/or the second temperature sensor etc. The valve arrangement 305 includes at least one or several valves of valve devices 305*a*-305*d*. However, the valve arrangement 305 may include more valves and valve devices as shown in FIG. 13. The heated purified fluid may then go via a first fluid path or second fluid path including a concentrate path 377*c* connecting a concentrate channel 306*b* of the EDI-device 306 with the tank 350.

According to one embodiment, the first fluid path comprises the EDI-device 306. The first fluid path then includes the product channel 306*a* (FIG. 4) of the EDI-device 306. In one embodiment, the first fluid path includes all of the channels of the EDI-device 306. Alternatively, the second fluid path comprises the EDI-device 306. The second fluid path then includes the product channel 306*a* (FIG. 4) of the EDI-device 306. In one embodiment, the second fluid path includes all the channels of the EDI-device 306.

In an alternative embodiment, the polisher device comprises a mixed bed filter device. Thus, in the embodiments herein described with reference to an EDI-device, the EDI-device is replaced with the mixed bed filter device.

After the actual disinfection of the water purification apparatus 300, the control unit 112 is configured to perform one or several post disinfection programs.

For example, the control unit 112 is configured to cause the water purification apparatus 300 to perform an active cool down of an RO-membrane 324 of the RO-device 301. The active cool down comprises to: control the RO-pump 450 to pump water from a water source 398 to the RO-device 301 until a predetermined cooling criterion for the RO, membrane 324 has been fulfilled. The active cool down further comprises to control the valve arrangement to drain reject fluid from the water purification apparatus 300, to the drain 339. The active cool down may include to close the permeate side of the RO-membrane 324, for example by closing the valve devices downstream the permeate outlet 301*b*.

In another example, the water purification apparatus 300 comprises a second pump 316 (see FIG. 13). The second pump may also be referred to as a chemical intake pump. The control unit 112 is in this embodiment configured to cause the water purification apparatus 300 to control the second pump 316 to pump air (i.e. from an air inflow, e.g. in the tank 350, backwards through the first recirculation path 381). The control unit 112 is further configured to control the valve arrangement 305 to direct the air past the closed product port 128 and/or past the closed drain port 118 of the water purification apparatus 300 in order to remove water from the port(s) 118, 128.

In a further exemplary embodiment, the second pump 316 is arranged to be used for pumping a cleaning agent such as citric acid. The control unit 112 is in this embodiment configured to cause the water purification apparatus 300 to control the second pump 316 to pump a cleaning agent into the feed fluid path 391, and to circulate the cleaning agent in the first reject recirculation path and the second reject recirculation path, from the reject outlet 301*c* to the feed inlet 301*a*, in order to remove scaling on an RO-membrane 324 of the RO-device 301.

FIG. 7 illustrates the third exemplary embodiment of a water purification apparatus 300, with fluid paths marked up for illustrating another example of a partial disinfection of the fluid path of the water purification apparatus 300. The differences in line style of the fluid paths illustrates the main flows in the first fluid path (thicker lines) and the second fluid path (dash double dot line), during the partial disinfection. In the third exemplary embodiment, there is no recirculation of fluid in order to heat the fluid, except for the minor flow from the concentrate channel 306*b* of the EDI-device 306 back to the tank 350 via the concentrate fluid path 377*c* (and in some cases also the minor flow from the electrode channel 306*c*). If the polisher device alternatively comprises a mixed bed filter device, there is no recirculation of fluid from the bed filter device. In the example of FIG. 7, the control unit 112 is configured to cause the water purification apparatus 300 to control heating, with the heater 302, of the purified fluid in the purified fluid path 371, in order to fulfil a temperature dependent disinfection criterion for the EDI-device 306. In response to the temperature dependent disinfection criterion for the EDI-device 306 is fulfilled, the control unit 112 is configured to control the water purification apparatus 300 to re-direct the heated purified fluid into a second fluid path, here including the bypass path 371*d* and the product fluid path 371*c*, and thereby to bypass the EDI-device 306. In response to the temperature dependent disinfection criterion for the EDI-device 306 being fulfilled, the control unit 112 is also configured to control heating, with the heater 302, of the purified fluid in the second fluid path in order to fulfil a temperature dependent disinfection criterion for the second fluid path. The heater 302 is here configured to heat the purified fluid in one step from about 20° C. to above 75° C.

The second fluid path comprises the ports 118, 128, which thus are in fluid communication with the second fluid path. The second temperature dependent disinfection criterion comprises to fulfil a temperature dependent disinfection criterion for the ports 118, 128. Further, the second fluid path also comprises the first drain path 384, and the second temperature dependent disinfection criterion then comprises to fulfil a temperature dependent disinfection criterion for the first drain path 384. Thus, the heated purified fluid is passed via the ports 118, 128 and via the first drain path 384 to drain 339. The temperature is measured in the first drain path 384, with the drain path temperature sensor 315. The temperature should thus be at least 75° C. for a certain predetermined time, in order to fulfil the respective A0 value for the ports 118, 128 and the first drain path 384. The second temperature dependent criterion for the port may also include to have a certain pressure of the fluid that flows past the port or ports 118, 128. The pressure is for example monitored with a pressure sensor 308 (see FIG. 13) in the product fluid path 371*c*, and controlled by means of the RO-pump 450 and/or the flow control device 305*a*.

Methods for Cleaning

In the following, a plurality of different cleaning programs will be explained, with reference to the flow charts of FIGS. 8-12, to the exemplary embodiments of the water purification apparatuses of FIGS. 5-7, and the detailed description of the water purification apparatus of FIG. 13.

In some embodiments, a cleaning program may start with one or several of the following starting programs:

Flushing of the RO-Membrane Reject Side, S1*a*

Flushing the RO-membrane reject side is performed to lower the concentrations of substances present after a treatment. As an explanation, when sending reject fluid back to the feed side of the RO-membrane 324, the reject fluid will get more and more concentrated up to a point where feed fluid, reject fluid and the amount of permeate fluid produced are in balance.

Flushing of the First Drain Path, S1*b*

Flushing the first drain path 384 is performed to remove as much of the residuals from the patient fluid that may be present. It is important to do this flush with cold water in order to get a best possible flush. If sending heated fluid directly, proteins may denaturate on the fluid path surfaces, thereby making them much harder to clean.

Cleaning First Drain Path with Cleaning Agent, S1*c*

In this program, a cleaning agent such as citric acid is distributed with the second pump 316, via a chemical intake path 382 (FIG. 13), to the first drain path 384, i.e. the patient drain path, including the patient conductivity sensor 336, at the same time as the first drain path 384 is flushed with cold water. To detect that the cleaning agent is taken in the conductivity sensor 336 is used. Both parallel paths 384, 384*a* should be filled with cleaning agent (FIG. 13). The drain line valve 341 is first open and the primary drain line valve 338 is closed. That enables the use of conductivity sensor 336 to detect when the cleaning agent has reached the drain 339. After filling with cleaning agent, the product water valve 305*d* is closed and all produced fluid is directed back to the tank 350. In one embodiment, the cleaning agent is active during the heating phase and disinfection phase of the purified fluid path 371 and will according to one embodiment not be flushed away until the port disinfection starts. The citric acid will act as an anti-scaling agent and also remove any residues left after the cold water flush. The citric acid will also have a disinfection effect, due to the low pH of the citric acid. The fluid present in the first drain path 384 stays there for performing its descaling and cleaning activity while the water purification apparatus 300 prepares for the heating disinfection phase.

When the optional starting programs are finished, the water purification apparatus 300 thus starts to prepare itself for heat disinfection:

In some embodiments, the preparations comprise controlling S2 the fluid level in the tank 350 to a predetermined level of the tank 350, before heating of the purified fluid starts. For example, the fluid level is controlled to an appropriate level such that, when the fluid in the tank 350 is heated, there is room for the fluid to expand without leaking out e.g. via tank air vent line 325. According to one embodiment, the inlet valve 332 and/or the tank valve 328 are closed when the predetermined level has been reached (see FIG. 13). Thereby no fresh cold water is introduced during the heating, e.g. during the recirculation for heating the fluid, and the fluid may be heated faster. The three-way valve 305*b* is set to direct all water back to the tank 350. Optionally, a reject bypass valve 321 is opened to bypass the restrictors of constant flow device 318, in order to reduce the pressure over the RO-membrane 324 (see FIG. 13).

After the optional preparations have been made, a method for cleaning the water purification apparatus 300 can be started. In the following, a plurality of different cleaning methods will be explained. In some embodiments, only heat disinfection is performed for cleaning the apparatus 300. Only one pump, thus the RO pump 450, is used to produce a flow for heat disinfecting the fluid paths of the apparatus 300 (except in embodiments when also the pump 316 is actuated to heat disinfect the fluid path the pump 316 is arranged to).

Complete Heat Disinfection

Methods for performing a complete disinfection will now be explained with reference to the flowcharts of FIGS. 8-12, and to the FIG. 5.

Many parts of the water purification apparatus 300 belong, as explained above, to the feed side of the water purification apparatus 300 (to the feed side of the RO-device 301) and fluid paths leading to this side. Thus, complete heat disinfection includes disinfecting those parts, and is done some days apart, typically twice a week. In one exemplary embodiment, the product channel 306*a* of the EDI-device 306 (FIG. 5) is always omitted, i.e. bypassed, during the complete heat disinfection. The reason is to protect the EDI-device 306 from metals that may pass the RO-membrane 324 while the RO-membrane 324 is heated up since the RO-membrane 324 gets more permeable as the temperature increases. These parts are taken care of during other disinfection phases, i.e. the ports and drain phase disinfection, as will be explained in the following. Further, if the polisher-device comprises a mixed bed filter device, the mixed bed filter device is always bypassed during the complete heat disinfection.

In the following two different complete disinfection programs will be explained: a Regular program and a Planned absence program.

1a. Regular Program

The regular program runs according to what is recommended by the RO-membrane manufacturer, i.e. not increasing the temperature more per unit time than recommended. Also, when lowering the temperature, the decrease needs to be less, per unit time, than a maximum defined by the manufacturer. The latter is included in active cool down. Specifically, the heating and cool down procedures are important for temperatures outside the normal operation range of the membrane, e.g. above 40° C. The active cool down will also reduce the time at high temperature for the RO-membrane, which will increase the lifetime of the RO-membrane.

The regular heat disinfection will now be explained. Steps done for risk mitigation, such as e.g. comparing flow sensors, testing that the fluid path does not leak, and so on, are here omitted for brevity, but could be included in the program.

Disinfection Starts—First Sequence

Before the program is started, the RO-pump 450 needs to be started such that fluid is pumped through the RO-membrane 324 via the heater 302. The method then comprises controlling S3 the heating of the purified fluid. For example, when the flow sensor 410 detects a flow, the heater 302 is switched on. Reference is now made to FIG. 5, where the first fluid path is indicated by the thick line from the permeate outlet 301b to tank 350 and further to the feed inlet 301a. The three-way valve 305c is controlled to direct the heated permeate fluid into the bypass path 371d. The three-way valve 305c is thus set to bypass the EDI-device 306. As will be further described below in relation to FIG. 13, the heated fluid is directed to the air trap chamber 319 and back to the tank 350 via the emptying valve 396.

The heater 302 is then set to deliver power in such amount that the temperature of the RO-membrane 324 does not increase faster than a predetermined rate, i.e. a predetermined number of degrees per unit time, e.g. 3° C./min, in order to not stress the RO-membrane 324. The predetermined rate is for example set by the supplier of the RO-membrane 324.

The method further comprises re-circulating S4 the heated purified fluid in the first fluid path until a first temperature dependent criterion is fulfilled S4d. For example, the method comprises measuring S4b the temperature of the purified fluid in the first fluid path, and/or measuring S4c a flow rate the purified fluid. The first temperature dependent criterion comprises, for example, controlling heating, based on the measured temperature, of the purified fluid such that a temperature of the purified fluid is within a range of 70°-95° Celsius. The temperature is in some embodiment set to be sufficient for disinfection of the first fluid path, or a component in the first fluid path. In other words, the first temperature dependent criterion comprises re-circulating the heated purified fluid in the first fluid path to the feed fluid path, until a first temperature dependent disinfection criterion is fulfilled. The temperature of the purified fluid may then be measured with the product fluid temperature sensor 313, and the temperature should reach a predetermined temperature sufficient for disinfection, e.g. 85° C.

In some other embodiments, the temperature of the purified fluid should reach a certain temperature, which corresponds to that the fluid in the tank 350 (and thus the RO-membrane 324) is pre-heated to a certain level, e.g. 40° C. The heating is also depending on the flow rate of the purified fluid. Thus, in some embodiment, the first temperature dependent criterion comprises to control heating and pumping with the RO-pump 450, based on the measured temperature and the measured flow rate in the permeate fluid path 371a, such that the purified fluid obtains a predetermined temperature dependent flow rate.

In another embodiment, the first temperature dependent criterion comprises to heat the RO-membrane 324 to a certain temperature for a certain time, e.g. such that an A0-criterion for the RO-membrane 324 is achieved. For example, the A0-criterion may include that the certain temperature is between 70-85° C., and the certain time is between 5 to 20 minutes. The A0-concept will be explained in more detail in the following.

If the first criterion S4d is not fulfilled, the control of the heating S3 and the re-circulating S4 is continued.

Disinfection Continues—Second Sequence

In response to the first temperature dependent criterion being fulfilled, the method comprises re-directing S5 the heated purified fluid to flow in a second fluid path of the water purification apparatus 300. The second fluid path may encompass one, several or all of the paths on the permeate side of the water purification apparatus 300. However, according to one embodiment, the product channel 306a of the EDI-device 306 may constantly be bypassed during a complete disinfection.

The method further comprises to control heating S6 of the redirected heated purified fluid, in order to fulfil a second temperature dependent disinfection criterion for the second fluid path. All paths need to reach a prescribed disinfection criterion, specific for that path or component in the path. The disinfection criterion includes, in some embodiments, to reach an A0-value that will be described in the following. This can be achieved by either continuously measuring the temperature at strategic points such as with the product fluid temperature sensor 313 and/or with a drain path temperature sensor 315 and calculate the A0-values, or use validated sequences to achieve the correct A0-values. In other words, the method comprises measuring S61a the temperature of the fluid in the second fluid path. In some embodiments, the method comprises determining, based on the measured temperature, a time duration for heat disinfecting the second fluid path with the fluid at the measured temperature, such that a bacterial reduction criterion is fulfilled, and controlling heat disinfection of the second fluid path based on the time duration. The second temperature dependent criterion then comprises to heat disinfect the second fluid path during the time duration. The time duration is for example calculated by using the A0-concept. Thereby, the required disinfection of the second fluid path, or a component of the second fluid path, can be achieved.

If the A0-values are calculated during the disinfection there is a possibility to minimize the energy consumption and time used for the disinfection program compared to a method which use validated sequences.

The method checks, for each second path, if the second criterion is fulfilled S61b. If not, the method continues to control heating S6 of the fluid in the second fluid path. If the second criterion is fulfilled for one second path, the method checks S61c if there are more second fluid paths to be disinfected. If so, the method re-directs S5 to the other second fluid path that is not yet disinfected, and controls heating S6 of the fluid in the second fluid path.

The disinfection is finished when the second criterion is fulfilled S61b for all paths on the permeate side. For example, if all prescribed A0-values for the second fluid paths have been met, the disinfection is finished.

In some embodiments, the method continues, after the disinfection is finished, to perform one or several post disinfection programs, e.g. an active cool down program and an emptying of ports of water program.

Active Cool Down Including Disinfection of Ports and Drain Path

Figure 11:
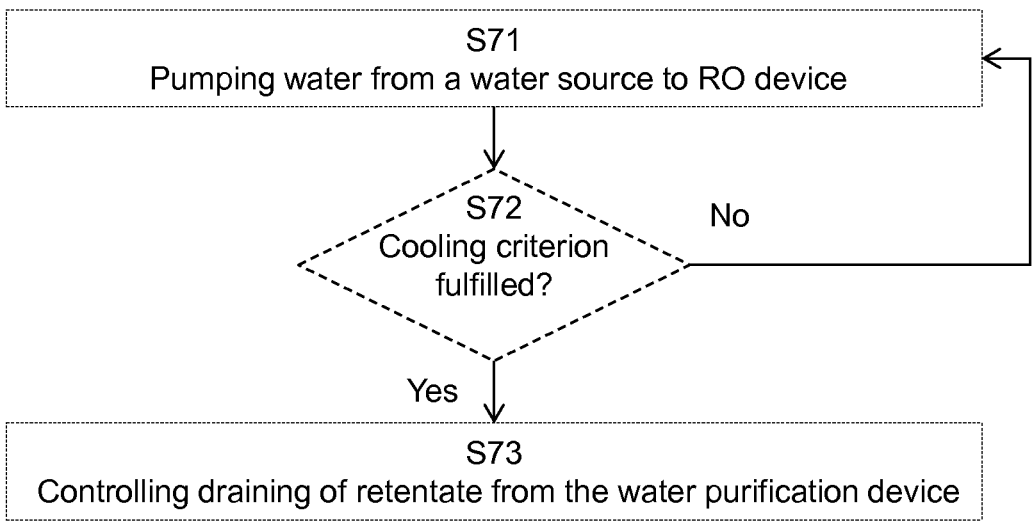

During the active cool down S7, illustrated in the flow chart of FIG. 11, inlet valve 332 and/or the tank valve 328 are opened to let cold water into the apparatus 300 again, and the three-way valve 305b is opened to drain 339 to let hot water to drain 339.

At the same time a partial disinfection program may be performed, in order to disinfect the ports 118, 128 and the first drain path 384, while bypassing the EDI-device 306. Also parts leading to the ports 118, 128 and the first drain path 384 are heat disinfected during the partial disinfection, such as product water valve 305d and the fluid path from the air trap chamber 319 to the product port 128 (see FIG. 13). During the partial disinfection program, heated purified fluid, e.g. 85° C. or above, is passed past the ports 118, 128 and further down through the first drain path 384 in order to disinfect the two paths 384, 384a herein (see FIG. 13). The level of disinfection is secured by the drain path temperature sensor 315. When sufficient disinfection of the ports 118, 128 and the first drain path 384 has been achieved the permeate side of the RO-membrane 324 is closed S64 and left to be cooled down. For further explanation, reference is made to the detailed description of partial disinfection further down, which embodiments also may be made in the complete disinfection programs.

The cool down of the RO-membrane 324 continues until an estimated temperature of below e.g. 40° C. on the reject side of the RO-membrane 324 has been reached. The estimation of the temperature is first based on the permeate flow temperature measured by permeate temperature sensor 303 and the energy needed to reach the temperature during the heating of the first drain path 384. By also knowing the amount of heated water sent to the second drain path 388 and what the temperature of the feed water measured by feed water temperature sensor 326 is, it is possible to estimate when the reject side temperature has become below 40° C. In other words, the active cool down comprises to pump S71 water from a water source to the RO-device 301 until a predetermined cooling criterion S72 for the RO-membrane 324 has been fulfilled, and to control draining S73 of reject fluid from the water purification apparatus 300.

After the active cool down program has been finished, an optional program for emptying the ports of water can be performed.

Emptying of Ports of Water (Optional)

Directly after having disinfected the ports and the first drain path 384, in parallel with the active cool down, the second pump 316 is started to pump air S8 (FIG. 10) in from the tank 350 (the surfaces of the tank 350 are still hot) and pumps it past the ports 118, 128 to remove any water from them. This step may be omitted for improved bacteriological status between treatments. However, the ports 118, 128 should then be emptied at the beginning of the start-up of the next treatment, before the patient is asked to attach the disposable line set 40.

After having finished the active cool down program, and optionally the emptying of ports and water program, the water purification apparatus 300 is for example set in a low power mode, e.g. to standby mode, or is shut down. The water purification apparatus 300 may also be configured to send a cleaning update S10 to the cycler 20.

1b. Planned Absence Program

The planned absence program is basically the same as the regular program. What differs are three phases:

1. The cool down program is not done. The water purification apparatus 1 is left for passive cool down to minimize the risk of bacteria's entering the fluid path. However, the partial disinfection including ports and drain path disinfection is done.
2. Emptying of the ports program is not done, for the same reason as for No. 1 above.
3. Chemical cleaning program for RO-membrane
   A small amount of a cleaning agent, corresponding to 0.3-1% of cleaning agent (e.g. 0.3-1% citric acid) in the reject paths 385b, 389, is introduced into the fluid path of the apparatus 300 by using the second pump 316. The permeate fluid is now heated using full power to the heater 302 into a heated purified fluid. Into this stream of heated purified fluid, the second pump 316 is pumping a small amount of cleaning agent, for example an amount of citric acid, e.g. 15 ml citric acid. When the cleaning agent has been transported to the tank 350 the permeate flow is stopped. The fluid in the tank 350 is now recirculated for a predetermined time in the feed/reject side loop while three-way valve 305b is closed to drain 339, so that the cleaning agent reaches all parts of the reject side and mainly the RO-membrane 324. In other words, the program includes circulating a cleaning agent S9 such as citric acid in a reject recirculation path from a reject outlet to the feed inlet of the RO-device, in order to remove scaling on an RO-membrane of the RO-device. During the recirculation, no fluid is passed through the RO-membrane 324 to the permeate side. The chemical cleaning program results in a descaling of the RO-membrane 324 in order to prevent buildups of scale on the RO-membrane 324 to, as far as possible, keep the performance of the RO-device 301 constant over time. The reason for not doing it is to minimize possible intake of bacteria. The cleaning agent may be left in the fluid path of the water purification apparatus 300 until next treatment is started.

The planned absence program is done prior to a planned pause in the use of the water purification apparatus 300, e.g. when the patient plans to be away from home for several days. Once the prescribed disinfection criterion has been met, e.g. a predetermined time at a temperature above a predefined temperature, the water purification apparatus 300 is set in e.g. a low power mode such as standby. By doing so, no living organisms should be present in the fluid path hence prolonging the time to when a new disinfection needs to be performed.

In one example embodiment, a complete cleaning of the water purification apparatus 300 comprises performing, in the specific order from a) to d):

a) Running a chemical cleaning program for descaling, and to some extent chemical disinfection, of the first drain path 384, including the patient conductivity sensor 336, with a cleaning agent such as citric acid;
b) Heat disinfecting the RO-membrane reject side, including the first recirculation path 381 and the second recirculation path 375 (essentially all fluid paths of the RO module and the post-treatment module except the first drain path 384, the last part of the product path and the EDI product channel 306a and the concentrate channel 306b).
c) Heat disinfection of the ports 118, 128 and the first drain path 384;
d) Running a chemical cleaning program including descaling of the RO-membrane 324 with a cleaning agent such as citric acid.

2. Partial Heat Disinfection Program

The partial heat disinfection program comprises disinfection of one or several of the EDI-device 306, the ports 118, 128, the drain paths 384, 388 and the parts leading to the ports 118, 128 and the first drain path 384, such as product water valve 305d and the fluid path from the air trap chamber 319 to the product port 128 (see FIG. 13). The partial heat disinfection program may also be referred to as a port and/or drain path disinfection program. In some embodiments, a partial heat disinfection program is done after every treatment, unless complete heat disinfection is done.

A plurality of different partial heat disinfection programs is possible, and in the following some alternatives will be explained.

As the complete programs, each partial heat disinfection program may start with flushing S1a the RO-membrane reject side and flushing Sib the first drain path 384 with cold water, to remove any substances present after a treatment.

Thereafter, some alternative partial heat disinfection programs are available:

Alternative 1

In this disinfection, the EDI product channel 306a and the concentrate channel 306b are included in the fluid path that is heat disinfected. This partial heat disinfection program is preferably run at the same frequency as the regular heat disinfection but at a different day. The main steps of this disinfection will be explained in the following. Steps done for risk mitigation, such as e.g. comparing flow sensors, testing that the fluid path does not leak, and so on are omitted.

As an optional pre-step, the water level in the tank 350 is controlled S2 by the water purification apparatus 300 to a predetermined level, e.g. up to its top level.

A plurality of different options for heating the EDI product water channel 306 is available:

Alternative 1—First Option

In a first sequence, feed water is pumped by the RO-pump 450 through the RO-device 301, and heating of the purified fluid is controlled S3 by controlling the power of the heater 302. The heated purified fluid is re-circulated S4 in a first fluid path including the first recirculation path 381 but with the EDI-device 306 bypassed via the bypass path 371d, as illustrated in FIG. 6 with a thick line. With reference to FIG. 13, the first fluid path comprises the permeate fluid path 371a, the polisher fluid path 371b, the product fluid path 371c up to the air trap chamber 319, and the first recirculation path 381 back to the tank 350 via the emptying valve 396. The method may include to control heating S3 and re-circulating S4 based by measuring S4b the temperature of the purified fluid in the first fluid path. The heating S3 and re-circulating S4 is then continued until a first temperature dependent criterion has been fulfilled. In one embodiment, the first temperature dependent criterion comprises controlling heating, based on the measured temperature, of the purified fluid, such that a temperature of the purified fluid is within a range of 70-95° Celsius. In some embodiment, this corresponds to that the fluid in the tank 350 and thus the RO-membrane 324 has been heated to approximately 40° C. Alternatively, the first temperature dependent criterion comprises to control heating of the purified fluid, and pumping with the RO-pump 450, based on the measured temperature and the measured flow rate of the purified fluid, such that the purified fluid obtains a predetermined temperature dependent flow rate. For example, the method comprises measuring S4b the temperature of the purified fluid in the first fluid path, and/or measuring S4c a flow rate of the purified fluid.

In a second sequence, when the water in the tank 350 add consequently also the ROU-membrane 324 have been heated to approximately 40° C. and thus fulfil a first temperature dependent criterion, the heated purified fluid is re-directed S5 to flow in a second fluid path, as indicated in FIG. 6 with the dash double dot line. The first temperature dependent criterion for example comprises controlling heating, based on the measured temperature, of the purified fluid such that a temperature of the purified fluid is within a range of 70-95° C. The heated purified fluid is then further heated S62a in order to fulfil a temperature dependent disinfection criterion of the EDI-device 306. When the temperature dependent disinfection criterion for the EDI-device 301 has been fulfilled S62c, which is e.g. determined by measuring S62b the temperature of the heated fluid passed in the product channel 306a, the method returns to step S5. The heated fluid is now re-directed to bypass the EDI-device 306, and thus into another second fluid path, that is the same as the previously mentioned second fluid path, except that the EDI-device 306 is now bypassed. The purified fluid is now continuously re-directed S5 to flow into the other second fluid path, and heated S6, until a second criterion for the second fluid path is fulfilled S61b. The second criterion for example comprises to fulfil the temperature dependent disinfection criterion for the port(s) 118, 128 and/or to fulfil a temperature dependent disinfection criterion for the first drain path 384. The method includes according to some embodiment, alternating the flow in the first drain path 384 between the conductivity drain path with the conductivity sensor 336 and the bypass path 384a. Any of the temperature disinfection criterions may include fulfilling a predetermined A0-criterion, e.g. an A0-value, for the EDI-device 306, for the port(s) 118, 128 or for the first drain path 384, respectively. In order to fulfil the A0-criterion, the temperature has to be measured. In other words, the method may comprise measuring S61a the temperature of the fluid in the second fluid path.

In some embodiments, the second temperature dependent criterion comprises determining, based on the measured temperature, a time duration for heat disinfecting the second fluid path with the fluid at the measured temperature, such that a bacterial reduction criterion is fulfilled, and controlling heat disinfection of the second fluid path based on the time duration. The time duration is for example an A0-value, expressed as a time duration Δt. Thereby, the required disinfection of the second fluid path, or a component of the second fluid path, can be achieved. If the temperature of the tank 350, i.e. the RO-membrane 324, becomes too low to achieve any of the disinfection criteria, the method returns to step S3 in order to heat the water in the tank 350 again.

Alternative 1—Second Option

The second option also includes a first sequence and a second sequence.

In the first sequence feed water is pumped by the RO-pump 450 through the RO-device 301, and heating of the purified fluid, by the heater 302, is controlled S3. The heated purified fluid is recirculated S4 in a first fluid path, including the second recirculation path 375 now including the EDI-device 306, as illustrated in FIG. 6 with a thick line. As will be further shown below with reference to FIG. 13, the first fluid path comprises the permeate fluid path 371a, the polisher fluid path 371b including the product channel 306a and the concentrate channel 306b, and the second recirculation path 375 back to the tank 350. The purified heated fluid is now passed from the reverse side of the product channel 306a of the EDI-device 306 back to the tank 350. Alternatively, the heated fluid is first recirculated in the first recirculation path 381 in order to heat the fluid to a predetermined temperature, e.g. 85° C., measured with the product fluid temperature sensor 313, corresponding to a temperature of the RO-membrane 324 of 40° C., before the heated fluid is passed through the EDI-device 306. The method then further comprises controlling heating S4a of the heated purified fluid that will flow through the EDI-device 306. The temperature is measured using the permeate temperature sensor 303. When the permeate temperature sensor 303 measures 35° C., the heater 302 is powered to heat the permeate fluid rapidly to between 70-85° C., in order to get a flow of as high temperature water through the product channel 306a of the EDI-device 306 as possible. Optionally, at the same time as the heater 302 is powered to heat rapidly, the reject side paths are opened maximally such that the recirculated reject fluid is mixed with recirculated heated purified fluid, while sending as much of the reject fluid as possible to drain 339, to thereby avoid that the RO-membrane 324 is heated above its temperature limit.

According to one embodiment, the EDI-device 306 is powered during heat disinfection thereof, in order to minimize decay of capacity of the EDI-device 306, and to minimize the time needed for subsequent recovery of capacity of the EDI-device 306 caused by the decay of capacity.

If the temperature of the fresh incoming water is as high as 35° C. already from the start, then the heating may need to be temporarily interrupted while lowering the temperature of the feed/reject side water. According to one embodiment, this is done by shutting off the heater 302 completely, while continuing to pump the mixed return and fresh water in the tank 350 to the reject side drain and recirculating the permeate water back to the tank 350 via a maximally open flow control device 305a. When the temperature measured by the permeate temperature sensor 303 has been lowered sufficiently (to not wait too long and getting too low temperature inside of the EDI product channel 306a) the heating of the EDI product channel 306a is restarted. The procedure may then need to be repeated one or more times. When the disinfection criterion for the EDI-device 306, e.g. the appropriate A0-value for the EDI-device, has been achieved, determined by means of measurements by the permeate temperature sensor 303, heating stops and the EDI product channel 306a is closed, i.e. by closing the valve device 307 (see FIG. 13). The EDI-device 306 is thereby bypassed. The heated purified fluid is now instead recirculated back to the tank 305 by opening the emptying valve 396, i.e. through the first recirculation path 381. The temperature of the heated purified fluid in the first recirculation path is controlled to have a temperature of 40° C., which is measured by the product fluid temperature sensor 313. In other words, the first criterion may comprise that: the disinfection criterion for the EDI-device 306 is fulfilled, the EDI-device 306 is bypassed, the heated purified fluid is recirculated through the first recirculation path 381 and the temperature is controlled to approximately 40° C.

In the second sequence, when the first criterion has been fulfilled, and thus the temperature of the heated purified fluid has reached a predetermined temperature of 40° C., the heated fluid is re-directed S5 to flow into a second fluid path including the ports 118, 128 and the first drain path 384, while heating S6 the purified fluid. The second predetermined criterion comprises to heat the purified fluid to a predetermined temperature to 85°, and then to direct the heated purified fluid to the different paths of the first drain path 384 in an alternating sequence, for example 1 minute in one path followed by 1 minute in the other path, until the entire first drain path 384 has reached the required A0-value. If the purified fluid cannot be heated to above 85°, e.g. in case the incoming water is so cold that the heater 302 cannot heat the purified fluid to above 75° C., measured with the product fluid temperature sensor 313, then the heated purified fluid is sent back to the tank 350 and the water purification apparatus 300 again controls the heater 302 to reach a temperature of 40° C. in the first sequence. As soon as this is achieved the heater 302 is again set to reach a temperature above 85° C. with the product fluid temperature sensor 313 and start sending the heated purified fluid past the port 118, 128 and to drain 339 in the second sequence. The temperature in the first drain path 384 is monitored by the drain path temperature sensor 315 such that the temperature in the first drain path 384 does not go below 65° C. (plus some margin). If so, a prolonged disinfection time is required for disinfecting the first drain path 384.

When the respective disinfection criterion has been fulfilled, the heat disinfection of the respective parts of the fluid path of the water purification apparatus 300 is considered finished.

In some embodiments, the heat disinfection is followed by a chemical cleaning program for the RO-membrane 324, as follows:

When the required disinfection has been reached, that is the respective disinfection criterions have been fulfilled, the three-way valve 317 is closed and the permeate flow is looped back to the tank 350 via the air trap chamber 319 and back to the tank 350 via the emptying valve 396. The permeate fluid is now heated, e.g. using full power to the heater 302, to obtain a heated purified fluid. The second pump 316 is pumping a small amount of cleaning agent into this stream of heated purified fluid. The small amount of cleaning agent is for example an amount of citric acid, e.g. 15 ml, for chemically cleaning the RO-membrane 324, as has previously explained in connection with the planned absence program.

An active cool down program to cool down the RO-membrane 324, as has been previously explained, may be performed simultaneously as any of the partial heat disinfection programs are performed.

After the heat disinfection, and optionally also the chemical cleaning program, is finished, the emptying the port(s) of water program may be run. After having finished the active cool down program, and optionally also the emptying the port(s) of water program, the water purification apparatus 300 is shut down.

Alternative 2

This alternative 2 is the same as alternative 1, except that the EDI product channel 306a is not included and thus not disinfected. Thus, the steps in alternative 1 describing how the product water channel 306 is heat disinfected are omitted in alternative 2. This partial heat disinfection program is preferably run after each use of the water purification apparatus.

Alternative 3

This alternative 3 is the same as alternative 2, but additionally includes the starting program Sic, explained in connection with the complete program, to use a cleaning agent before heating starts, to remove/avoid build ups of possible "deposits" (protein, calcium . . . ) in the first drain path 384, before the partial heat disinfection starts. It should be run as often as is needed to make sure the first drain path 384 is clean, thereby minimizing the risk of an altered conductivity cell (CP) constant of the conductivity sensor 336.

Alternative 4

Figure 12:
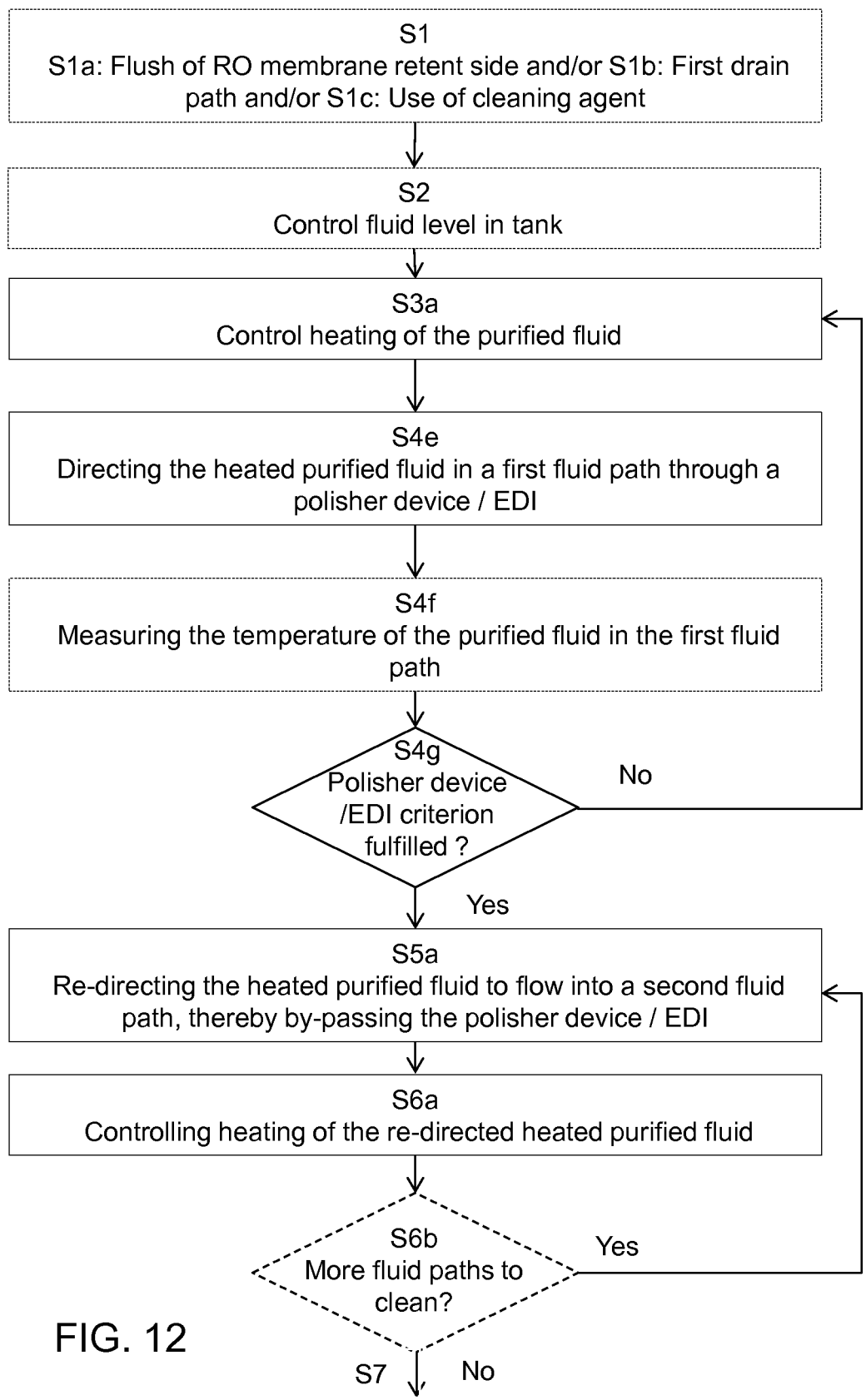

An alternative partial disinfection method is illustrated in FIG. 7 and in the flowchart of FIG. 12. The method may start with the same steps S1 and S2 as have been previously explained. The method comprises, in a first sequence, controlling eating S1a of the purified fluid produced by the RO-device 301, and directing S4e the heated purified fluid in a first fluid path, through a product channel of an electrodeionization unit, EDI-device, wherein the EDI-device also comprises a concentrate channel 306b. The temperature of the purified fluid is for example measured S4f by permeate temperature sensor 303 or product fluid temperature sensor 313. The first fluid path is in FIG. 7 illustrated with a thicker line.

In response to a temperature dependent disinfection criterion for the EDI-device being fulfilled S4g, a second sequence starts. The second sequence comprises re-directing S5a the heated purified fluid into a second fluid path to bypass the EDI-device 306 and to control S6a heating of the re-directed purified fluid, in order to fulfil a temperature dependent disinfection criterion for the second fluid path. The second fluid path is in FIG. 7 illustrated with the dash double dot line. The second temperature dependent disinfection criterion comprises, for example, to fulfil a temperature dependent disinfection criterion for the port(s) 118, 128 in the second fluid path. Alternatively or additionally, the second temperature dependent disinfection criterion comprises to fulfil a temperature dependent disinfection criterion for the first path.

The method thereafter checks if there are more fluid paths to clean S6b. If there are more fluid paths to clean, then the method returns to S5a. If there are no more fluid paths to clean, the method may perform any of the steps illustrated in the flowchart of FIG. 10.

The methods have been explained with reference to having an EDI-device. However, as an alternative, the EDI-device is in the above described methods replaced with a mixed bed filter device. The criteria described with reference to the EDI-device are then exchanged with criteria for a mixed bed filter device.

Extended Use of Disposable Line Set

In an alternative embodiment, a method for providing extended life of disposable line set 40 is proposed. Here, the disposable line set 40 is used with cycler 20 for more than one treatment. Instead of removing the disposable line set 40, a cleaning agent such as an agent inhibiting microbiological growth is pumped from container 392 and diluted in water purification apparatus 300. The diluted agent is pumped into the disposable line set 40 including cassette 42, its line portions and container 62 connected to the cassette 42. The agent, may in one embodiment be or include citric acid, or a deviation thereof, and may be pumped from container 392 and diluted in a portion of the fluid path of water purification apparatus 300 and then pushed into the circuit of disposable line set 40, for example via water line 64 (64a, 64b). In an alternative embodiment, the patient line 50 may be connected to a port of water purification apparatus 300 to receive the diluted agent to protect the circuit of disposable set 40. Further, alternatively, container 392 may be in direct fluid communication with the cycler 20, for example, via a connection to the patient line 50. Control unit 22 causes citric acid (or other suitable acid with or without additives) to be withdrawn from the container 392 and be directed inside cassette 42, lines connected thereto and container 62.

Control unit 22 is in one embodiment programmed to perform one or more mixing step, so that the agent inhibiting microbiological growth is diluted with the fluid already contained in the fluid line set 40, which may be sterilized product water using the above process to enable the circuit of disposable set 40 to be used for more than one treatment instead of being disposed after a one single use.

In one embodiment, diluted agent is left in the semi-disposable circuit (e.g., circuit of disposable set 40) until a start of preparation for a next treatment. Here, control unit 22 performs a rinsing step to remove the diluted agent from the semi-disposable circuit; the rinsing may be done with sterilized product water from water purification apparatus 300.

It should be appreciated that the above-described procedure is not a disinfection procedure; rather, the procedure with citric acid act as a bacteriostatic solution and avoid growth in-between treatments to enable extended use of cassette 42, associated lines and container 62. It should also be appreciated that if traces of the citric acid remain in the circuit of disposable set 40, the minor amount would not harm the patient considering that a citric acid cycler is a common and safe cellular metabolism.

Hot Water Disinfection of Semi-Disposable Line Set

In an alternative multiple use of disposable line set 40 embodiment, the anti-growth inhibiting agent just described is replaced by hot water disinfection. Before the disposable line set 40 is heat disinfected, the disposable line set 40 may be flushed with cold water, i.e. product water produced with the water purification apparatus 300 without heating the water, in order to move away any residuals from the previous treatment. Thereafter, the heater 302 of water purification apparatus 300, under control of control unit 112, heat its water to 70° C. for example to heat disinfect the fluid path of the water purification apparatus 300. As illustrated herein, water purification apparatus 300 is connected to disposable line set 40 via water line segment 64a having sterilizing grade filters 70a and 70b. Sterilizing grade filters 70a and 70b include endotoxin removal capacity to help produce sterilized product water. The sterilized product water is used to dilute the concentrates to prepare ready to use dialysis fluid. The capacity of disposable filters 70a and 70b depends upon the bioburden of the water supplied by water purification apparatus 300. Pumping heated water through sterilizing grade filters 70a and 70b therefore disinfects the filters, placing them in better shape for performing multiple treatments using the same disposable set 40. Pumping heated water through disposable set 40 also disinfects the disposable set, placing it in better shape for multiple treatments. In one embodiment, the heated fluid used for cleaning the disposable line set 40 includes the cleaning agent. Thereby a combined effect of heat disinfection and cleaning with the cleaning agent may be achieved.

The A0 Concept

The heat disinfection programs are in some embodiments based on following principle. Heating aims at preventing growth of bacteria (and thus biofilm) on the internal surfaces of the water purification apparatus fluid path. In order to achieve a sufficient reduction of organisms a concept herein referred to as the "A0 concept" is used. The concept is defined as:

$$A_0 = \Sigma 10^{(T-80)/z} \cdot \Delta t \qquad \text{Equation (2)}$$

where z is a value defined by the type of microorganisms that need to be killed. For bacterial spores, which are the most resistant of all microorganisms, a z-value of z=10° C. is considered needed. At a temperature T of 80° C. the A0 expresses the time, $\Delta t$ in seconds, needed to reach an expected effect. If T=90° C. only a tenth of the time is needed, i.e. 6 seconds to get an A0 of 60. If T is instead 70° C. the time needed is tenfold.

In a setting where more than one patient is subjected to the same instrument or device it is recommended to achieve an A0-value of more than 3000*. This is thus the minimal value needed when performing a reconditioning of the water purification apparatus 300 when being moved from one patient to the next.

During periods when the water device is being used by only one patient an A0-value of 600* should be sufficient. The point of the fluid path that reaches the lowest temperature is the one for which the A0 should be determined.

The effectiveness of the disinfection is measured by calculation of A0. All temperatures above 65° C. are considered having "disinfection effect". This means that every instance of temperatures above 65° C., i.e. during heat up and cool down, should be included in the calculation of A0. Therefore, the expression above could alternatively be written as:

$$A_0 = \int_{\tilde{t} \in t(T>65[°C.])} 10^{(T(\tilde{t})-80)/z} \cdot d\tilde{t} \qquad \text{Equation (3)}$$

meaning that all time, thus every time point, for which the temperature is above 65° C. are accounted for. Thus, any of the criteria referred to herein, may include an A0-criterion according to the A0-concept.

*Numbers are found in an article "Thermal Disinfection—The A0 Concept and the Biological Background" by Urs Rosenberg, volume 11, 2003. References are in this article done to prEN14476 and prEN15883.

Detailed Description of a Water Purification Apparatus

FIG. 13 illustrates an example embodiment of the water purification apparatus 300. In other embodiments, the water purification apparatus 300 may include less or more components or modules. The water purification apparatus 300 of FIG. 13 receives water from a water source 398 (FIG. 3), such as a continuous source of potable or drinkable water from a patient's home. In various embodiments, water purification apparatus 300 may be installed in a room having access to the water source 398 to provide WFPD to cycler 20 as discussed herein. The water is optionally filtered using a particle pre-filter 334 to remove dirt and sediment, before it is delivered to the water purification apparatus 300. The water enters the water purification apparatus 300 via the water inlet port 333. As previously described, the water purification apparatus 300 includes a pre-treatment module 160, a RO module 170 and a post-treatment module 180. The pre-treatment module 160 includes a particle filter and an activated carbon filter, i.e. an activated carbon bed, to further remove contaminants and impurities. The particle filter and the activated carbon filter are embodied in one single filter package 331. The single package 331 is a disposable package. The pre-treatment module 160 includes an inlet valve 332 and a constant flow device 330 upstream the filter package 331. The inlet valve 332 controls the feed water inflow by control of the control unit 112. The constant flow device 330 provides a constant flow to the tank 350 providing that the water pressure is above a minimum pressure for constant flow device 330. Further, pre-treatment module 160 comprises a sampling valve 329 with a sampling port outlet 329a, a tank valve 328, a pre-treatment conductivity sensor 327 and a feed water temperature sensor 326 downstream the filter package 331. The sampling port outlet 329a allows a sample to be taken from the feed water, e.g. to test the chlorine level. The tank valve 328 controls the flow of filtered feed water to the tank 350. The pre-treatment conductivity sensor 327 monitors the conductivity of the filtered feed water, and the feed water temperature sensor 326 monitors the temperature of the filtered feed water. The temperature of the filtered feed water is for example needed to calibrate the conductivity measurement of the filtered feed water. The described components are included in a pre-treatment fluid path 390. The pre-treatment fluid path 390 is connected to the water inlet port 333 and ends into the tank 350. The inlet valve 332 and the tank valve 328 are configured to be controlled by the control unit 112 of the water purification apparatus 300. Water softening in the pre-treatment module 160 may alternatively or additionally be achieved using lime softening, ion-exchange resins or an anti-scalant such as polyphosphate, as known in the art. It should be appreciated that the filter package 331 is in some embodiments not required and may not be present.

The RO module 170 comprises the tank 350, the RO-pump 450 and the RO-device 301. A RO-device 301 has already been described in detail with reference to the FIG. 5 and reference is made to that description for further explanation. The filtered (or unfiltered) feed water enters the tank 350, for example from an upper part of the tank 350. Feed water is accumulated in the tank 350 and pumped by the RO-pump 450 to the feed inlet 301a (see FIGS. 5-7) of the RO-device 301.

Empty, low and high-level switches 350a, 350b, 350c provided in tank 350 detect its water level, while a computer program run on a control unit 112 of water purification apparatus 300 is configured to control the opening and closing of inlet valve 332 and tank valve 328, which are open during the filling of tank 350, and closed when the water level in tank 350 activates its high-level switch 350c connected to control unit 112. Inlet valve 332 opens again when the water level falls below low-level switch 350b of tank 350, thus tripping the low-level switch 350b connected to control unit 112. If the water level in the tank 350 rises too high, excess water is drained via a tank air vent line 325 and tank air vent 335 (overflow connection), e.g. to a tray 420 or drain 339. The tank air vent 335 is accessible from outside the water purification apparatus 300. The tank air vent 335 may be closed e.g. during transport of the water purification apparatus 300, such that any water in the tank 350 will be prevented to flow to the tray 420 and cause water to flow out of the water purification apparatus 300.

The control unit 112 is configured to cause RO-pump 450 to stop pumping, if empty level switch 350a in tank 350 detects air or a critically low water level. RO-pump 450 is configured to provide the water flow and pressure requisite for the reverse osmosis process taking place at RO-device 301. As previously described e.g. with reference to FIG. 5, the RO-device 301 filters water to provide purified water at its permeate outlet 301b. Reject water leaving RO-device 301 at a reject outlet 301c (may be fed back into RO-pump 450 to conserve water consumption or alternatively be pumped to drain 339.

Purified water leaving the RO-device 301 is transported in a purified fluid path 371 inside the water purification apparatus 300 before being output through a product port 128, thus a water outlet. The purified fluid path comprises permeate fluid path 371a, polisher fluid path 371b and product fluid path 371c. The EDI-device 306 may be by-passed via the bypass path 371d. The bypass path 371d is connected to the fluid path upstream the EDI-device 306, and to the fluid path downstream the EDI-device 306. Purified water leaving the RO-device 301 passes a flow sensor 410, a heater 302, and a permeate temperature sensor 303, included in the permeate fluid path 371a. The flow sensor 410 monitors the flow of the purified fluid leaving the RO-device 301. The heater 302, heats, by control of the control unit 112, the purified water leaving the RO-device 301. The permeate temperature sensor 303 monitors the temperature of the purified fluid leaving the RO-device 301 directly downstream the heater 302. An additional conductivity sensor 304 monitors the conductivity of purified water leaving RO-device 301.

Downstream the heater 302, the permeate temperature sensor 303 and the additional conductivity sensor 304, the purified fluid enters the post-treatment module 180 via the polisher fluid path 371b. The post-treatment module 180 comprises the polisher device, e.g. the EDI-device 306. The three-way valve 305c is arranged to be controlled by the control unit 112 to selectively direct the purified fluid flow into either the EDI-device 306, or into the bypass path 371*d* in order to bypass the EDI-device 306. When directed to the EDI-device 306, the purified fluid enters the product channel 306*a*, the concentrate channel 306*b* and the electrode channel 306*c* of the EDI-device 306. The purified fluid is fed to all the channels via the polisher fluid path 371*b* downstream the three-way valve 305*c*. The EDI-device 306 is configured to produce product water. The produced product water leaves the EDI-device 306 and enters the product fluid path 371*c*. A product channel valve 307 regulates the flow rate of the product water in the product fluid path 371*c* from the product channel 306*a*. The concentrate fluid path 377*c* is arranged to pass concentrate water and the electrode fluid back to the tank 350.

The product water is passed to the product port 128, and further into a thereto connected water line 64 (64*a*, 64*b*) of the fluid line set 40 for transport to the point of care. The fluid line set 40 comprises two sterile sterilization filters 70*a*, 70*b*. The sterile sterilization filters 70*a*, 70*b* filter the product water leaving the product port 128 into sterilized product water, that is suitable for injection. According to some alternative embodiments those filters are left out or the number of filters is less or more than two.

A drain port 118 defines a first drain path 384 to the drain 339. A drain line 56 of the fluid line set 40 is connected to the drain port 118, in order to pass fluid, such as used PD-fluid, from the drain port 118 to the drain 339. The first drain path 384 here embodies the part of a cycler drain path that is present inside the water purification apparatus 300. The first drain path 384 comprises a conductivity sensor 336, a drain path temperature sensor 315 and a drain line valve 341. The conductivity sensor 336 is configured to measure the conductivity of the fluid in the drain path. The temperature sensor 315 is arranged to measure the temperature of the fluid in the first drain path 384. The drain line valve 341 is, by control of the control unit 112, arranged to regulate the flow in the first drain path 384 through the conductivity sensor 336. The first drain path 384 further comprises a bypass path 384*a* arranged to by-pass the conductivity sensor 336, the drain path temperature sensor 315 and the drain line valve 341. The bypass path 384*a* comprises a valve 340. The valve 340 is arranged to regulate the flow through the bypass path 384*a*.

The flow control device 305*a* is configured to control the flow rate of purified water in the recirculation path 315 arranged from a point downstream the heater 302, the permeate temperature sensor 303 and the additional conductivity sensor 304, and back to the tank 350. A product water pressure sensor 308 is arranged to monitor the pressure in the product fluid path 371*c* downstream the EDI-device 306. A product water flow sensor 309 is arranged to monitor the flow rate of the product water downstream the EDI-device 306. The pressure and the flow rate of the product water are feed to the control unit 112. The control unit 112 is configured to control the operation of the flow control device 305*a*. More particularly the control unit is configured to regulate the flow rate in the recirculation path 375 based on the pressure and flow rate of the product water, in order to control the flow rate of the product water to a desired flow rate, and the pressure of the product water to a desired pressure. The flow control device 305*a* is for example a motorized flow control valve that is configured to finely regulate the flow rate in the recirculation path 375.

A product water valve 305*d* is arranged to, by control of the control unit 112, control the produced product flow to go to either the product port 128, or back to the tank 350 via an additional recirculation path, here a first recirculation path 381. An emptying valve 396 is arranged to control the flow rate in the first recirculation path 381. The first recirculation path 381 is fluidly connected to the product fluid path 371*c* via an air-trap chamber 319. A product water conductivity sensor 312 is arranged to monitor the conductivity of the product water upstream the air-trap chamber 319. A product fluid temperature sensor 313 is configured to monitor the temperature of the product water upstream the air-trap chamber 319.

In operation, a portion of the rejected water leaving the RO-device 301 via a fluid path 385*a* passes an auxiliary constant flow device 318, which provides a steady flow of rejected water to a three-way valve 305*b* (e.g. a three-way solenoid valve) under control of control unit 112. A remaining portion of the rejected water returns to RO-pump 450 via a valve 320 (e.g., a manual needle valve) in a first reject path 385*b*. Three-way valve 305*b* is configured to selectively divert the rejected water either to drain 339 via a second drain path 388 or back to tank 350 via a second reject path 389. A bypass-path 385*f* is arranged to bypass the auxiliary constant flow device 318. A reject bypass valve 321 is arranged to control the flow in the bypass path 385*f* by control of the control device 112.

All meters and sensors described in connection with water purification apparatus 300 in FIG. 13 are in some embodiments configured to send their corresponding signals to control unit 112.

The water purification apparatus 300 includes a container 392 containing a microbiological growth inhibiting agent. As illustrated, container 392 is in fluid communication with an inlet 392*a* of the water purification apparatus 300. In FIG. 13, the chemical intake path 382 connects container 392 to the fluid path of the water purification apparatus 300. Alternatively, container 392 may be connected via a line (not illustrated) leading directly to disposable cassette 42 operating with cycler 20, or be connected to water line 64, or be connected to drain line 56.

The agent inhibiting microbiological growth in the container 392 may be a suitable physiologically safe acid, such as citric acid, citrate, lactic acid, acetic acid, or hydrochloric acid (or a combination thereof). In one embodiment, container 392 contains citric acid, citrate or a derivative thereof. It is noted that container 392 may also include additives provided together with the acid (such as with citric acid). The chemical inlet 392*a*, is located for example at the front of water purification apparatus 300. A presence sensor (not shown, e.g. an optical sensor) is arranged to sense when the container 392 is connected to the chemical inlet 392*a*. The three-way valve 317, under control of control unit 112, at chemical inlet 392*a* is arranged to open towards a second pump 316 being a chemical intake pump and tank 350. The second pump 316 is arranged to feed disinfecting solution into tank 350. The optical sensor is arranged to detect if the source of cleaning or disinfection solution is connected or disconnected. If/when the container 392 is removed or is not detected by the optical sensor, the second pump 316 is stopped or not activated and three-way valve 317 is closed towards the chemical inlet 392*a*. Three-way valve 317 under control of control unit 112 may also be used to recirculate water and disinfectant from and to tank 350 during the phases of chemical disinfection (i.e. disinfection with a cleaning agent), cleaning and/or rinse. The second pump 316 and a valve 310 are arranged in a path 379 fluidly connecting the three-way valve 317 and the product fluid path 371*c*. The valve 310 is arranged to control the flow in the path 379. In one embodiment, when the first recirculation path 381 is disinfected for example during a complete disinfection, the heated fluid is also passed through a path 386 between the first recirculation path 381 and the three-way valve 317, through the path 379 and to the recirculation path 381. During this flow the second pump 316 is active and thus pumps the heated fluid to not stop the flow.

In a more detailed disinfection phase example, when chemical disinfection is initiated, the level in tank 350 is adjusted to a level just above low-level switch 350*b*. Control unit 112 causes RO-pump 450 to start and run until empty-level switch 350*a* indicates a presence of air. RO-pump 450 is then stopped and inlet valve 332 is opened. Inlet valve 332 is maintained open until empty-level switch 350*a* indicates water. Second pump 316 is then run until a preset amount of chemical solution is metered into tank 350. When the level in tank 350 reaches a pre-determined level, the three-way valve 317 is opened to drain 339. RO-pump 450 circulates the fluid in the fluid path during the chemical intake phase and may be operated in two directions to create turbulent flow and to increase disinfection time and contact. At the end of the intake phase, reject bypass valve 321 is opened and the three-way valve 305*b* is actuated to open second drain path 388 to drain 339 and to drain the water level in tank 350 to its low-level switch 350*b*.

The described pre-treatment module 160, the RO module 170 and post-treatment module 180, are enclosed inside of a single water purification cabinet 110*a*, except for the filter package 331, which is removably arranged, e.g. hinged, on the outside of the single water purification cabinet 110*a*. The filter package 331 may then be exchanged when exhausted. In an alternative embodiment, the modules may be arranged in separate units. As mentioned above, purified water is sent from water purification apparatus 300 to disposable set 40 via water line 64. Referring to FIG. 1, water line 64 feeds purified water to a water port 282 of cassette 42 of disposable set 40. Water line 64 is in one embodiment a flexible tube having a first end connected to the product port 128 of the water purification apparatus 300 and a second end connected to a water port 282 of the cycler 20. Water line 64 may be at least 2 meters long and in one embodiment longer than 4 meters. Water line 64 allows water purification apparatus 300 to be installed in a room having an available water source, while cycler 20 resides in a different room in which the patient resides, e.g., sleeps. Water line 64 may accordingly be as long as necessary to connect water purification apparatus 300 to cycler 20.

FIG. 13 also illustrates that the disposable line set 40 includes a drain line 56 configuration arranged to conduct fluid, such as used dialysis fluid, to the drain 339 of the water purification apparatus 300. Drain line 56 is e.g. a tube having a first end connected to cassette 42 of cycler 20 and a second end including a drain line connector 58 (FIG. 1) connected to a drain port 118 of the water purification apparatus 300. Drain line 56 may alternatively be a flexible tube, which may be more than 2 meters long and in some embodiments longer than 4 meters. Drain line may be as long as necessary to connect between water purification apparatus 300 and cycler 20. Water line 64 and drain line 56 in the illustrated embodiment run parallel using dual lumen tubing. It is also possible that water purification apparatus 300 and cycler 20 are positioned close together, such that the same two line fluid path including water line 64 and drain line 56 may for example be less than 0.5 meters. Moreover, while a dual lumen water line 64 and the drain line 56 are illustrated, it is possible that water line 64 and drain line 56 are separate.

A water tray 420 is positioned below the water purification apparatus 300. A liquid sensor 370 is arranged at the bottom of the water tray 420 to detect any leakage from the water purification apparatus 300. In one example embodiment, the water tray 420 is enclosed inside the purification cabinet 110*a* of the water purification apparatus 300.

Figure 14:
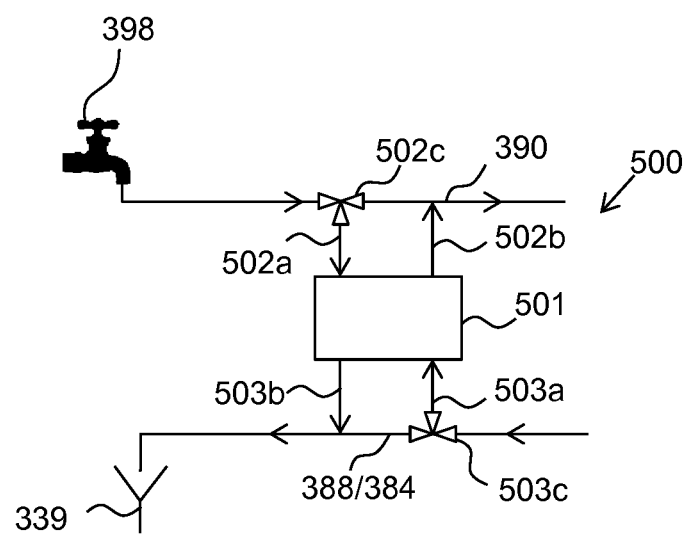
FIG. 14 illustrates an embodiment of a heat conserving arrangement.

FIG. 14 illustrates a heat conserving arrangement 500 according to one example embodiment. The heat conserving arrangement 500 is arranged to transfer thermal energy, i.e. heat, from the fluid in the first drain path 384 and/or the fluid in the second drain path 388, to another medium such as the fluid in the pre-treatment fluid path 390. Thereby thermal energy from the drained fluid is conserved to the water in the pre-treatment fluid path 390, and less energy is needed for any subsequent heating of the water for heat disinfection, provide a certain temperature of the product water or providing a constant temperature of the RO-membrane. The heat conserving arrangement 500 comprises a heat conserver 501, a first path 502*a*, a second path 502*b*, a third path 503*a* and a fourth path 503*b*. A three-way valve 502*c* is arranged to, under control of the control unit 112, direct water from the feed fluid path 391 to the heat conserver 501 via the first path 502*a*. A second path 502*b* directs heated water from the heat conserver 501 back to the feed fluid path 391. A three-way valve 503*c* is arranged to, by control by the control unit 112, direct fluid from any of the drain paths 384, 388 to the heat conserver 501 via the third path 503*a*. A fourth path 503*b* directs cooled fluid from the heat conserver 501 back to drain paths 384, 388, and further to drain 339.

Alternatively, the heat conserving arrangement 500 is arranged to transfer thermal energy, i.e. heat, from the fluid in the first drain path 384 to the reject fluid from the RO-device 301 in any of the fluid path 385*a*, the second drain path 388, the first reject path 385*b*, or the second reject path 389, or to the fluid in the tank 350, or to the feed fluid in the feed fluid path 391. In one embodiment, the second drain path 388 is arranged as a cooling coil around part of the first drain path 384 inside the apparatus 300. In another embodiment, the reject fluid that is passed to drain 339 via the second drain path 388 is guided via a further line fluidly connected to the second drain path 388 to the conserving arrangement 500 and thereafter via another line to the fluid in the pre-treatment fluid path 390. A valve may control the flow in the second drain path 388 downstream the connection to the line that guides reject fluid to the conserving arrangement 500, and another valve may control the flow in the further line that guides reject fluid to the pre-treatment fluid path 390.

Optionally, a fan may be arranged to further cool the reject fluid flow leaving the apparatus 300 via the second drain path 388 and/or the drain fluid leaving the apparatus via the first drain path 384.

The heat conserver 501 comprises for example a passive or active heat transfer element, e.g. a heat exchanger or a Peltier element. In one embodiment, the heat conserver 501 comprises a conserving element, e.g. a closed container or fluid path with another medium such as another fluid, which absorbs the heat and thus thermal energy from the fluid in any of the drain paths 384, 388. The absorbed thermal energy may be transferred to the fluid in the pre-treatment fluid path, 390 or the reject fluid at any time, or be released to the surroundings. In one embodiment, the heat conserver 501 comprises a fluid accumulator where some of the fluid from any of the drain paths 384, 388 is collected, for future transfer of heat from the fluid to the water in the feed fluid path 391 or the first reject path 385*b*. The closed container and the fluid accumulator are in one embodiment insulated in order to prevent heat loss. For example, they may be insulated in order to keep the heat for up to 24 h with minimal loss. The heat can then be used for heating up the water in the pre-treatment fluid path 390 in the next treatment saving energy, or simply released to the surroundings. Further, if thermal energy in the drain fluid is reduced the drained fluid will become less hot, which reduces the risk for the operator interacting with the drain paths 388, 384 to become burnt by the hot drain fluid. The function can be bypassed in phases when it is not used, by controlling the three-way valves 502c, 503c. The second path 502b and the fourth path 503b in some embodiments include valves (not shown), controllable by the control unit 112, to restrict the flows in the same. The heat conserving arrangement 500 may be included inside the cabinet 110a of the water purification apparatus 300. According to another embodiment, the heat conserving arrangement 500 is arranged outside the cabinet 110a of the water purification apparatus 300.

The present disclosure is not limited to the above-described preferred embodiments. Various alternatives, modifications and equivalents may be used. Therefore, the above embodiments should not be taken as limiting the scope of the disclosure, which is defined by the appending claims.

The invention claimed is:

1. A water purification apparatus for producing purified water, the water purification apparatus comprising:
 a reverse osmosis device arranged to produce a purified fluid flow and a reject fluid flow, the reverse osmosis device comprising a feed inlet, a permeate outlet, and a reject outlet,
 a feed fluid path arranged with a reverse osmosis pump to pump feed fluid to the feed inlet,
 a heater arranged to heat the purified fluid produced by the reverse osmosis device downstream from the reverse osmosis device,
 a first fluid path arranged to circulate heated purified fluid from a point downstream from the heater to a tank arranged in the feed fluid path inside the water purification apparatus,
 a second fluid path arranged to transport the heated purified fluid inside the water purification apparatus;
 a valve arrangement arranged to direct the heated purified fluid into the first fluid path or the second fluid path, and
 a control unit configured to control cleaning of the water purification apparatus, the control unit being configured to cause the water purification apparatus to:
  control heating, with the heater, of the purified fluid from the reverse osmosis device,
  control the valve arrangement to re-circulate the heated purified fluid in the first fluid path until a first temperature dependent criterion is fulfilled,
  control the valve arrangement to re-direct the heated purified fluid to flow in the second fluid path of the water purification apparatus in response to the first temperature dependent criterion being fulfilled, and
  control heating, with the heater, of the re-directed heated purified fluid in order to fulfill a second temperature dependent disinfection criterion for the second fluid path.

2. The water purification apparatus according to claim 1, wherein the first temperature dependent criterion is a first temperature dependent disinfection criterion.

3. The water purification apparatus according to claim 1, further comprising a temperature sensor arranged to measure a temperature of the purified fluid in the first fluid path, wherein the first temperature dependent criterion includes a temperature of the purified fluid being within a range of 70°-95° Celsius.

4. The water purification apparatus according to claim 3, further comprising a first flow sensor arranged to measure a flow rate of the purified fluid, wherein the first temperature dependent criterion includes the purified fluid obtaining a predetermined temperature dependent flow rate.

5. The water purification apparatus according to claim 1, further comprising a temperature sensor arranged to measure a temperature of the purified fluid in the second fluid path, wherein the control unit is configured to:
 determine, based on the temperature measured by the temperature sensor, a time duration for heat disinfecting the second fluid path with the purified fluid at the temperature such that a bacterial reduction criterion is fulfilled, and
 control heat disinfection of the second fluid path based on the time duration to fulfill the bacterial reduction criterion.

6. The water purification apparatus according to claim 1, further comprising a port in fluid communication with the second fluid path, the port being arranged to be connected to a fluid line set, wherein the second temperature dependent disinfection criterion includes a temperature dependent disinfection criterion for the port.

7. The water purification apparatus according to claim 1, wherein the second fluid path includes a first drain path, and wherein the second temperature dependent disinfection criterion is a temperature dependent disinfection criterion for the first drain path.

8. The water purification apparatus according to claim 1, wherein the first fluid path or the second fluid path includes a polisher device, and wherein the control unit is configured to cause the water purification apparatus to:
 control heating of the purified fluid that flows through the polisher device such that a temperature dependent disinfection criterion for the polisher device is fulfilled, and
 control the water purification apparatus to bypass the polisher device in response to the temperature dependent disinfection criterion for the polisher device being fulfilled.

9. The water purification apparatus according to claim 1, wherein the control unit is configured to cause the water purification apparatus to control a fluid level in the tank to a predetermined level of the tank before controlling the heater to heat the purified fluid.

10. The water purification apparatus according to claim 1, wherein the control unit is configured to cause the water purification apparatus to:
 control the reverse osmosis pump to pump water from a water source to the reverse osmosis device until a predetermined cooling criterion for a reverse osmosis membrane of the reverse osmosis device has been fulfilled, and
 control the valve arrangement to drain reject fluid from the water purification apparatus.

11. The water purification apparatus according to claim 1, wherein the water purification apparatus includes a second pump, and wherein the control unit is configured to cause the water purification apparatus to:
 control the second pump to pump air, and
 control the valve arrangement to direct the air past a closed port of the water purification apparatus in order to remove water from the port.

12. The water purification apparatus according to claim 1, wherein the water purification apparatus includes a second pump arranged for pumping a cleaning agent, and wherein the control unit is configured to cause the water purification apparatus to:
    control the second pump to pump the cleaning agent into the feed fluid path, and
    circulate the cleaning agent in a reject recirculation path from the reject outlet to the feed inlet in order to remove scaling on a reverse osmosis membrane of the reverse osmosis device.

13. The water purification apparatus according to claim 1, wherein the permeate outlet of the reverse osmosis device is fluidly coupled to a permeate fluid path arranged such that it is in contact with the heater in order to heat the purified fluid produced by the reverse osmosis device.

14. The water purification apparatus according to claim 1, further comprising a heat conserving arrangement arranged to transfer heat to another medium from at least one of a fluid in a first drain path and a fluid in a second drain path.

15. The water purification apparatus according to claim 1, further comprising a disposable line set in fluid communication with the water purification apparatus, wherein the control unit is configured to cause the water purification apparatus to clean the disposable line set.

16. A method for cleaning a water purification apparatus configured to produce purified water, the water purification apparatus including a reverse osmosis device configured to produce a purified fluid flow and a reject fluid flow, the method comprising:
    controlling heating of purified fluid in the purified fluid flow downstream from the reverse osmosis device,
    re-circulating the heated purified fluid in a first fluid path from a point downstream from a heater to a tank arranged in a feed fluid path upstream from the reverse osmosis device until a first temperature dependent criterion is fulfilled,
    re-directing the heated purified fluid to flow in a second fluid path of the water purification apparatus in response to the first temperature dependent criterion being fulfilled, and
    controlling heating of the re-directed heated purified fluid such that a second temperature dependent disinfection criterion for the second fluid path is fulfilled.

17. The method according to claim 16, wherein the first temperature dependent criterion is a first temperature dependent disinfection criterion.

18. The method according to claim 16, wherein controlling heating of the purified fluid and re-circulating the heated purified fluid includes measuring a temperature of the purified fluid in the first fluid path, and wherein the first temperature dependent criterion includes a temperature of the purified fluid being within a range of 70°-95° Celsius.

19. The method according to claim 18, wherein controlling heating of the purified fluid and re-circulating the heated purified fluid includes measuring a flow rate of the purified fluid, and wherein the first temperature dependent criterion includes the purified fluid obtaining a predetermined temperature dependent flow rate.

20. The method according to claim 16, wherein controlling heating of the re-directed heated purified fluid includes measuring the temperature of the re-directed heated purified fluid in the second fluid path, and wherein the method further comprises:
    determining, based on the measured temperature, a time duration for heat disinfecting the second fluid path with the re-directed heated purified fluid at the measured temperature such that a bacterial reduction criterion is fulfilled, and
    controlling heat disinfection of the second fluid path based on the time duration to fulfill the bacterial reduction criterion.

21. The method according to claim 16, wherein the water purification apparatus comprises a port in fluid communication with the second fluid path, the port being arranged to be connected to a fluid line set, and wherein the second temperature dependent disinfection criterion includes a temperature dependent disinfection criterion for the port.

22. The method according to claim 16, wherein the second fluid path includes a first drain path, and wherein the second temperature dependent disinfection criterion is a temperature dependent disinfection criterion for the first drain path.

23. The method according to claim 16, wherein the first fluid path or the second fluid path includes a polisher device, and wherein the method comprises:
    controlling heating of the purified fluid that flows through the polisher device such that a temperature dependent disinfection criterion for the polisher device is fulfilled, and
    controlling the water purification apparatus to bypass the polisher device in response to the temperature dependent disinfection criterion for the polisher device being fulfilled.

24. The method according to claim 16, further comprising controlling a fluid level in the tank to a predetermined level of the tank before heating of the purified fluid.

25. The method according to claim 16, further comprising:
    pumping water from a water source to the reverse osmosis device until a predetermined cooling criterion for a reverse osmosis membrane of the reverse osmosis device has been fulfilled, and
    controlling a valve arrangement to drain reject fluid from the water purification apparatus.

26. The method according to claim 16, further comprising pumping air past a closed port of the water purification apparatus in order to remove water from the port.

27. The method according to claim 16, further comprising circulating a cleaning agent in a reject recirculation path from a reject outlet of the reverse osmosis device to a feed inlet of the reverse osmosis device in order to remove scaling on a reverse osmosis membrane of the reverse osmosis device.

28. The method according to claim 16, further comprising transferring heat to another medium from at least one of a fluid in a first drain path and a fluid in a second drain path.

29. The method according to claim 16, further comprising cleaning a disposable line set in fluid communication with the water purification apparatus.

30. A non-transitory, computer-readable medium storing instructions, which when executed by a processor, cause the processor to:
    control heating of purified fluid in a purified fluid flow downstream from a reverse osmosis device in a water purification apparatus,
    re-circulate in the water purification apparatus the heated purified fluid in a first fluid path from a point downstream from a heater to a tank arranged in a feed fluid path upstream from the reverse osmosis device until a first temperature dependent criterion is fulfilled,
    re-direct the heated purified fluid to flow in a second fluid path of the water purification apparatus in response to the first temperature dependent criterion being fulfilled, and control heating of the re-directed heated purified fluid such that a second temperature dependent disinfection criterion for the second fluid path is fulfilled.

\* \* \* \* \*